(12) United States Patent
Miyata et al.

(10) Patent No.: US 8,999,725 B2
(45) Date of Patent: Apr. 7, 2015

(54) METHOD OF MEASURING EXTERNAL STIMULUS AND VOLUME CHANGE USING STIMULUS-RESPONSIVE GEL COMPRISING EDANS

(75) Inventors: Takashi Miyata, Suita (JP); Tadashi Uragami, Suita (JP); Kaori Okawa, Gifu (JP)

(73) Assignee: Japan Science and Technology Agency, Saitama (JP)

(*) Notice: Subject to any disclaimer, the term of this patent is extended or adjusted under 35 U.S.C. 154(b) by 1894 days.

(21) Appl. No.: 11/919,133

(22) PCT Filed: Apr. 24, 2006

(86) PCT No.: PCT/JP2006/308556
§ 371 (c)(1),
(2), (4) Date: Oct. 24, 2007

(87) PCT Pub. No.: WO2006/118077
PCT Pub. Date: Nov. 9, 2006

(65) Prior Publication Data
US 2010/0063771 A1 Mar. 11, 2010

(30) Foreign Application Priority Data

Apr. 28, 2005 (JP) ................................. 2005-133431

(51) Int. Cl.
*G01N 21/76* (2006.01)
*G01N 21/64* (2006.01)
*G01N 21/77* (2006.01)

(52) U.S. Cl.
CPC .......... *G01N 21/643* (2013.01); *G01N 21/6452* (2013.01); *G01N 21/77* (2013.01); *G01N 2021/7723* (2013.01)

(58) Field of Classification Search
CPC .......... G01N 2021/7723; G01N 21/80; G01N 33/538; G01N 1/405; A61L 27/34; A61L 31/10; A61L 27/52; A61L 15/60
See application file for complete search history.

(56) References Cited

U.S. PATENT DOCUMENTS

| | | |
|---|---|---|
| 5,015,843 A | 5/1991 | Seitz et al. ................ 250/227.21 |
| 5,854,078 A | 12/1998 | Asher et al. |

(Continued)

FOREIGN PATENT DOCUMENTS

| | | |
|---|---|---|
| JP | 11-228850 | 8/1999 |
| JP | 2000-266676 | 9/2000 |

(Continued)

OTHER PUBLICATIONS

McCurley, "An optical biosensor using a fluorescent, swelling sensing element", Biosensors & Bioelectronics, 1994, v. 9, pp. 527-533.*

(Continued)

*Primary Examiner* — Yelena G Gakh
(74) *Attorney, Agent, or Firm* — Harness, Dickey & Pierce, P.L.C.

(57) ABSTRACT

In one embodiment of the present application, a stimulus-responsive gel is disclosed with optical characteristic molecule introduced therein that is capable of easily and securely converting a volume change responding to external stimulus to optical data being easy to handle in the construction of sensor system; an external stimulus measuring apparatus making use of the same; and a method of measuring external stimulus therewith. A molecule having fluorescent chromophore or a molecule or a molecule capable of absorbing visible light or ultraviolet light is introduced in a stimulus-responsive gel so that the content of the molecule having fluorescent chromophore or the molecule or a molecule capable of absorbing visible light or ultraviolet light falls within such a range that the concentration of the molecule having fluorescent chromophore or a molecule or the molecule capable of absorbing visible light or ultraviolet light in the stimulus-responsive gel with optical characteristic molecule introduced therein is substantially proportional to the fluorescence intensity or absorbance of the visible light or ultraviolet light of the stimulus-responsive gel with optical characteristic molecule introduced therein.

6 Claims, 14 Drawing Sheets

(56) References Cited

U.S. PATENT DOCUMENTS

| | | | |
|---|---|---|---|
| 5,898,004 A | 4/1999 | Asher et al. | |
| 6,268,092 B1 | 7/2001 | Akashi et al. | |
| 2002/0068019 A1 | 6/2002 | Fujiwara et al. | 422/82.05 |

FOREIGN PATENT DOCUMENTS

| | | |
|---|---|---|
| JP | 2001-33832 | 2/2001 |
| JP | 2002-174597 | 6/2002 |
| JP | 2002-201366 | 7/2002 |
| JP | 2003-113249 | 4/2003 |
| JP | 2003-147210 | 5/2003 |
| JP | 2004-027195 | 1/2004 |
| JP | 2005-010490 | 1/2005 |
| WO | WO 03/083454 | 10/2003 |

OTHER PUBLICATIONS

John H. Holtz et al. "Polymerized colloidal crystal hydrogel films as intelligent chemical sensing materials." Nature, vol. 389, Oct. 23, 1997, pp. 829-832.

Kaori Okawa et al. "Fluorescence Resonance Energy Transfer in Hydrogels Having Chromophore." Polymer Preprints, Japan vol. 53, No. 1, 2004, pp. 1799, and partial English translation thereof.

Kaori Okawa et al. "Fluorescence Resonance Energy Transfer in Hydrogels Having Chromophore." Polymer Preprints, Japan vol. 53, No. 2, 2004, pp. 4936-4937, and partial English translation thereof.

Kaori Okawa et al. "Properties of Fluorescence Resonance Energy Transfer in Hydrogels Having Chromophore." Abstract of Symposium Organized by Research Group on Polymer Gels, 2005, pp. 67-68, and partial English translation thereof.

European Search Report for 06732267.7 dated May 9, 2012.

\* cited by examiner

METHOD OF MEASURING EXTERNAL STIMULUS AND VOLUME CHANGE USING STIMULUS-RESPONSIVE GEL COMPRISING EDANS

TECHNICAL FIELD

The present invention relates to a stimulus-responsive gel with optically active molecules introduced therein, an external stimulus measuring apparatus making use of the same, and a method of measuring an external stimulus. The stimulus-responsive gel is capable of easily and surely converting into optical data a volume change caused by an external stimulus.

BACKGROUND ART

Stimulus-responsive gels, which change their volumes by swelling or shrinking according to an external stimulus (pH, temperature, ionic concentration, etc.) given thereon, are highly promising as sensor elements and the like. Conventionally, evaluations of the volume changes have been carried out mainly by volumetric measurement using microscopy, weight measurement using a scale or the like. Such methods are difficult to use for actually constructing a new system using such a stimulus-responsive gel.

A system has been reported recently, which uses a stimulus-responsive gel which makes use of a structural color produced from fine particles such as silica particles arrayed inside the stimulus-responsive gel, thereby to overcome such a problem (see Non-Patent Citation 1, Patent Citation 1, etc., for example). In this method, an external stimulus changes a swelling ratio of the stimulus-responsive gel, thereby to change intervals between the silica particles. The changes in the intervals cause changes in wavelength and intensity of the structural color. In this way, the volume change is converted into an optical change. Moreover, similar structural color can be obtained by forming holes arrayed in order by dissolving away such fine particles arrayed in a stimulus-responsive gel. A system using such a method to convert a volume change to an optical change has been also reported (see Patent Citation 2, for example).

Moreover, even though it does not concern conversion of a volume change in a stimulus-responsive gel to optical data, optical devices and sensors have been reported, which changes light transmittance by a volume change in stimulus-responsive gel particles arrayed between two transparent boards, the volume change being caused by light irradiated on the stimulus-responsive gel particles (for example, Patent Citations 3, 4, 5, and 6, etc.). These reports describe use of the stimulus-responsive gel particles in which color materials are dispersed. The arts described in the reports make use of the phenomenon in which when the stimulus-responsive gel particles are swollen, the gap between the two boards is filled with the swollen stimulus-responsive gel particles. As a result, the entire light will be absorbed by the pigment or the like in the gel particles, thereby causing a coloring state. On the other hand, when the gel particles are shrunk, the gel particles occupies very small portion of the gap between the two boards, whereby the most of the light will not be absorbed therein and pass therethrough, thereby causing a colorless state.

[Patent Citation 1]
Japanese Translation of PCT International Application, Toku-hyo, No. 2001-505236 (published on Apr. 17, 2001)
[Patent Citation 2]
Japanese Unexamined Patent Application Publication, Toku-kai, No. 2004-27195 (published on Jan. 29, 2004)
[Patent Citation 3]
Japanese Unexamined Patent Application Publication, Toku-kai, No. 2000-266676 (published on Sep. 29, 2000)
[Patent Citation 4]
Japanese Unexamined Patent Application Publication, Toku-kaihei, No. 11-228850 (published on Aug. 24, 1999)
[Patent Citation 5]
Japanese Unexamined Patent Application Publication, Toku-kai, No. 2001-33832 (published on Feb. 9, 2001)
[Patent Citation 6]
Japanese Unexamined Patent Application Publication, Toku-kai, No. 2005-10490 (published on Jan. 13, 2005)
[Non-Patent Citation 1]
J. H. Holtz, S. A. Asher, Nature, 389, 829-832 (1997)

DISCLOSURE OF INVENTION

Technical Problem

However, the conventional arrangement has a difficulty of converting the volume change of the stimulus-responsive gel into optical data easily and certainly.

That is, in the stimulus-responsive gel in which the silica particles are filled as described in Patent Citation 1 and Non-Patent Citation 1, and the stimulus-responsive gel having orderly-arranged holes prepared by dissolving silica particles from a stimulus-responsive gel in which the silica particles are orderly arranged, it is necessary to arrange the silica particles strictly in order during the synthesis of the gel. Thus, these arts are not easy and certain. Moreover, in the stimulus-responsive gel in which the silica particles are filled, it is necessary to fill the stimulus-responsive gel with the silica particles in a large quantity. This would deteriorate stimulus-responsive gel per se qualitatively.

As to the arts reported in Patent Citations 3, 4, 5, and 6, which use stimulus-responsive gel particles in which color materials used in optical elements or sensors are utilized, these arts simply utilize the fact that swelling of stimulus-responsive gel particles between two boards results in absorption of a large amount of light in the pigment or the like. These arts are capable of qualitatively detecting the volume change from the amount of light absorbed, but cannot convert into optical data the volume change of the stimulus-responsive gel in response to the external stimulus.

The present invention was accomplished in view of the above-mentioned problems. An object of the present invention is to provide a stimulus-responsive gel, which is capable of easily and certainly converting into optical data its volume change caused by an external stimulus, and an external stimulus measuring apparatus and an external stimulus measuring method using the same.

Technical Solution

In order to attain the object, an optically active molecule-introduced stimulus-responsive gel (hereinafter sometimes referred to simply "stimulus-responsive gel") according to the present invention changes its volume in response to an external stimulus and comprises optically active molecules. The optically active molecules can be molecules having fluorescence chromophores, or molecules capable of absorbing visible light or ultraviolet light; and the molecules having the fluorescence chromophores, or the molecules capable of absorbing visible light or ultraviolet light are contained in the stimulus-responsive gel in such a quantitative range that concentration of the molecules having the fluorescence chromophores, or of the molecules capable of absorbing visible light or ultraviolet light is substantially proportional to fluorescence intensity or absorbance of the visible light or ultraviolet light in the stimulus-responsive gel.

The stimulus-responsive gel is preferably arranged such that the concentration of the molecules having the fluorescence chromophores, or the molecules capable of absorbing the visible light or the ultraviolet light in the stimulus responsive gel is in a range between about 0.001% w/w to about 10% w/w relative to the dried weight of the stimulus-responsive gel comprising the optically active molecules.

The stimulus-responsive gel according to the present invention is preferably arranged such that the molecules having the fluorescence chromophores, or the molecules capable of absorbing the visible light or the ultraviolet light are introduced in the stimulus-responsive gel via chemical bonding. The stimulus-responsive gel according to the present invention may be arranged such that the molecules having the fluorescence chromophores, or the molecules capable of absorbing the visible light or the ultraviolet light are introduced in the responsive gel via an electrostatic interaction or hydrogen bonding.

The stimulus-responsive gel according to the present invention is preferably arranged such that the stimulus-responsive gel changes its volume by swelling or shrinking in response to the external stimulus by absorbing or discharging a liquid, which is water or an organic solvent. Moreover, the liquid which is absorbed or discharged by the stimulus-responsive gel when it changes its volume by swelling or shrinking in response to the external stimulus may be an organic solvent.

The stimulus-responsive gel according to the present invention is preferably arranged such that the external stimulus is pH, ionic concentration, heat, electricity, recognizable molecule, magnetic field, or light.

An external stimulus measuring apparatus according to the present invention includes at least: a sample section including: a stimulus-responsive gel according to the present invention; and a liquid, which the stimulus-responsive gel absorbs or discharges in response to an external stimulus, the sample section exposing the stimulus-responsive gel to the external stimulus so as to cause a volume change therein; and an optical data measuring section for irradiating light of a particular wavelength on the sample section and measuring fluorescence intensity or absorbance of the visible light or ultraviolet light.

The external stimulus measuring apparatus according to the present invention preferably further includes: an optical data outputting section for converting into an electric signal the fluorescence intensity or absorbance of the visible light or ultraviolet light measured by the optical data measuring section, and for outputting the electric signal.

The external stimulus measuring apparatus according to the present invention preferably further includes: a computing section for calculating out, from the electric signal outputted from the optical data outputting section, how large the external stimulus is, which causes the volume change in the stimulus-responsive gel.

It is preferable that the computing section store an analytical curve therein, which indicates how large the external stimulus is in correspondence to how large the fluorescence intensity or absorbance of the visible light or ultraviolet light is.

The external stimulus measuring apparatus according to the present invention is preferably arranged such that the external stimulus is pH, ionic concentration, heat, electricity, recognizable molecule, magnetic field, or light.

A method according to the present invention for measuring an external stimulus is a method including: (a) determining an analytical curve, which indicates how large an outer stimulus is according to fluorescent intensity, or absorbance of visible light or ultraviolet light, by (i) exposing to external stimuli of different known degrees a stimulus-responsive gel according to the present invention, in the presence of a liquid, which is absorbed in or discharged out of the stimulus-responsive gel in response to the external stimuli, so as to cause volume changes in the stimulus-responsive gel, (ii) irradiating the light of a particular wavelength on the stimulus-responsive gel exposed to the respective external stimuli of different known degrees, and (iii) measuring fluorescence intensity or absorbance of visible light or ultraviolet light therein; (b) (i) exposing to an external stimulus of an unknown degree the stimulus-responsive gel in the presence of the liquid, (ii) irradiating the light of the particular wavelength on the stimulus-responsive gel exposed to the external stimuli of the unknown degree, and (iii) measuring the fluorescence intensity or the absorbance of the visible light or the ultraviolet light in the stimulus-responsive gel; and (c) determining how large the external stimulus of the unknown degree is, from the measured fluorescence intensity or the absorbance of the visible light or ultraviolet light by using the analytical curve.

Effect of the Invention

A stimulus-responsive gel according to the present invention is a stimulus-responsive gel, which changes its volume in response to an external stimulus, and in which optically active molecules are introduced, wherein the optically active molecules are a molecules having a fluorescence chromophores, or molecules capable of absorbing visible light or ultraviolet light; and the molecules having the fluorescence chromophores, or the molecules capable of absorbing visible light or ultraviolet light are contained in the stimulus-responsive gel in such a quantitative range that concentration of the molecules having the fluorescence chromophores, or of the molecules capable of absorbing visible light or ultraviolet light is substantially proportional to fluorescence intensity or absorbance of the visible light or ultraviolet light in stimulus-responsive gel. Thus, the stimulus-responsive gel according to the present invention does not require tedious processes such as arranging particles in the stimulus-responsive gel in order. The stimulus-responsive gel according to the present invention can be produced by introducing the molecules having the fluorescence chromophores, or the molecules capable of absorbing visible light or ultraviolet light, into the stimulus-responsive gel during production of the stimulus-responsive gel. By such a simple and certain manner, the present invention makes it possible to convert into optical data the volume change in the stimulus-responsive gel. Moreover, the stimulus-responsive gel will not be qualitatively deteriorated so much because the quantity of the introduced molecules having the fluorescence chromophores or absorbing visible light or ultraviolet light is so small.

For a fuller understanding of the nature and advantages of the invention, reference should be made to the ensuing detailed description taken in conjunction with the accompanying drawings.

BEST MODE FOR CARRYING OUT THE INVENTION

Figure 1:
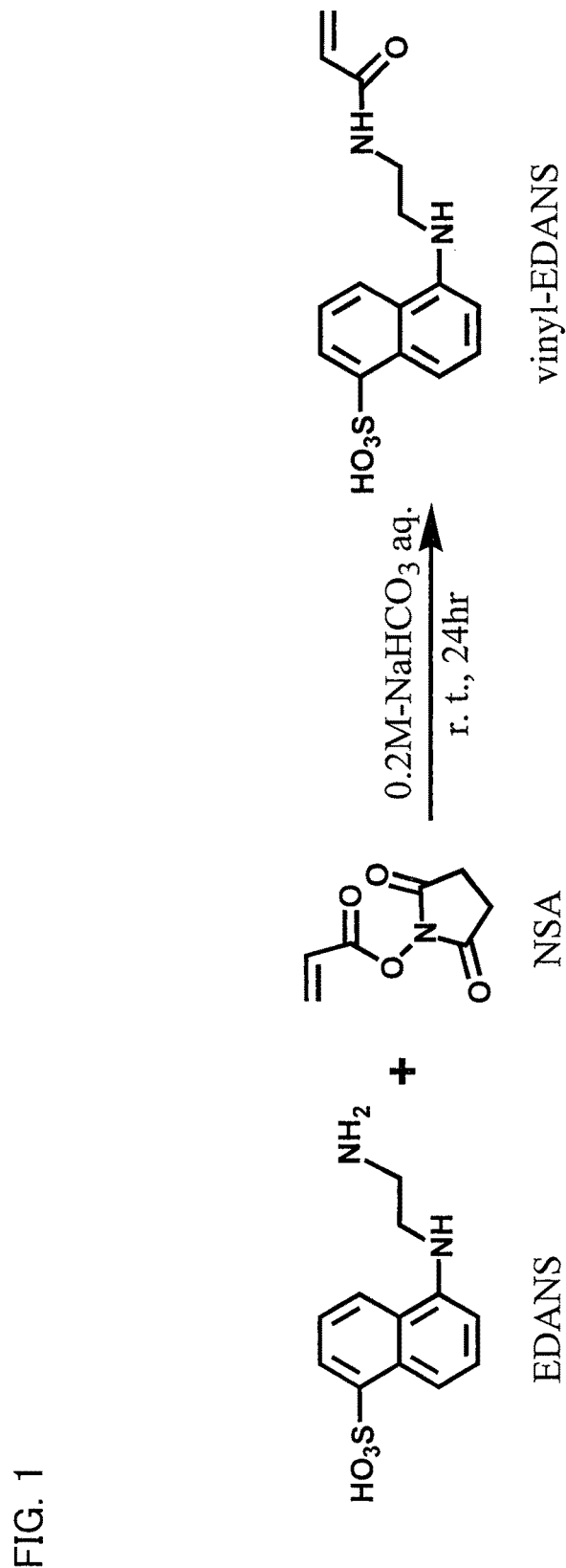
FIG. 1 is a view illustrating a chemical reaction formula for synthesis of vinyl group-introduced 5-(2'-aminoethyl)aminonaphthalene-1-sulfonic acid (EDANS) in Examples.

As a result of diligent studies to attain the object, the inventors of the present invention noticed importance of a proportional relationship between fluorescence intensity and a concentration of molecules having a fluorescent chromophores or between absorbance and a concentration of molecules capable of absorbing visible light or ultraviolet light, in order to convert the volume change of a stimulus-responsive gel into optical data easily and certainly. The inventors of the present invention expected that it is possible to convert into optical data a volume change of a stimulus-responsive gel by detecting the volume change as fluorescence intensity change or the absorbance change. The stimulus-responsive gel has optically active molecules introduced therein, which molecules have fluorescence chromophores or absorbs visible light or ultraviolet light and which molecules change their concentration in proportion with the fluorescence intensity or absorbance. The inventors of the present invention actually produced a stimulus-responsive gel with optically active molecules introduced therein, which molecules have fluorescence chromophores, and measured a volume change at various ion concentrations thereby to find a relationship between fluorescence intensity and the volume change. As a result, the inventors of the present invention found that there is a linear relationship in plotting logarithms of the volume change against logarithms of the fluorescence intensity. Moreover, because the linear relationship in plotting the logarithms of the volume change against the logarithms of the fluorescence intensity in the stimulus-responsive gel, it is expected that there is linear relationship in plotting the logarithms of the volume change against the logarithms of the absorbance in a stimulus-responsive gel with optically active molecules introduced therein, which molecules absorb visible light or ultraviolet light. Based on this knowledge, the inventors of the present invention found that by detecting volume change as a change in fluorescence intensity or absorbance, it is possible to convert into optical data an external stimulus-caused volume change in a stimulus-responsive gel with optically active molecules introduced therein, which molecules have fluorescence chromophores or absorb visible light or ultraviolet light. Accordingly, the inventors of the present invention found that it is possible to measure an external stimulus by measuring fluorescence intensity or absorbance in the stimulus-responsive gel of the present invention with optically active molecules introduced therein. The present invention was accomplished based on these findings. In the following, (I) the stimulus-responsive gel of the present invention with optically active molecules introduced therein, (II) an external stimulus measuring apparatus, (III) a method of measuring an external stimulus.

(I-1) Stimulus-Responsive Gel of the Present Invention

The stimulus-responsive gel of the present invention with optically active molecules introduced therein changes its volume by and according to an external stimulus. Here, the optically active molecules are molecules having fluorescence chromophores or a molecules capable of absorbing visible light or ultraviolet light.

The stimulus-responsive gel absorbs or discharges a liquid in response to an external stimulus such as pH, ionic concentration, heat, electricity, a recognizable molecule, magnetic field, light, or the like, thereby to change its volume. The volume change in the stimulus-responsive gel may reversibly or irreversibly occur in response to the external stimulus, but it is preferable that the volume change be reversible, because this allows the gel to be used repeatedly and gives the gel higher reproducibility as a sensor material.

The volume change in the stimulus-responsive gel of the present invention may occur to any extent. It is preferable that the volume change occur to a greater extent. It is more preferable that the volume change occur to cause a volumetric ratio of 2 or more between swelling and shrinking. It is further preferable that the volume change occur to cause a volumetric ratio of 5 or more between swelling and shrinking. It is especially preferable that the volume change occur to cause a volumetric ratio of 10 or more between swelling and shrinking. With the arrangement in which the volume change occurs to cause a volumetric ratio of 2 or more, the change in the concentration of the molecules having the fluorescence chromophores or absorbing the visible light or the ultraviolet light can be detected more sensibly in response to the volume change in the stimulus responsible gel. As a result, it is possible to convert the volume change into the optical data more sensibly. Moreover, as the volume change occur to a larger extent, the change in the concentration of the molecules having the fluorescence chromophores or absorbing the visible light or the ultraviolet light becomes larger, thereby attaining a higher sensitively. Therefore, this arrangement is preferable.

Moreover, the stimulus-responsive gel of the present invention comprises optically active molecules, that is, the molecules having the fluorescence chromophores or the molecules capable of absorbing the visible light or ultraviolet light. With this arrangement, the volume change occurred in the stimulus-responsive gel in response to the external stimulus can be converted into the optical data by detecting the fluorescence intensity or the absorbance of the visible light or the ultraviolet light.

It is preferable that the molecules having the fluorescence chromophores or the molecules capable of absorbing the visible light or the ultraviolet light be contained in the stimulus-responsive gel of the present invention in such a quantitative range that the concentration of these molecules in the stimulus-responsive gel is substantially proportional to the fluorescence intensity or the absorbance of the visible light or the ultraviolet light in the stimulus-responsive gel. With such a quantitative range, the fluorescence intensity or the absorbance of the visible light or the ultraviolet light in the stimulus-responsive gel is proportional to the concentration of these molecules in the stimulus-responsive gel. Because the molecules having the fluorescence chromophores or the molecules capable of absorbing the visible light or the ultraviolet light is constant in quantity, the volume change causes a change in concentration thereof. This makes it possible to convert the volume change in the optical data accurately. Patent Citations 3 and 5 describe that the concentration of the color material is equal to or more than a saturate absorbance concentration, which is such a high color material concentration that the color material concentration and the light absorbance amount are in such a relationship that is far different from a linear relationship. On the centrally, the present invention utilizes such a linear relationship.

There is no particular limitation as to how many molecules having the fluorescence chromophores or absorbing the visible light or the ultraviolet light the stimulus-responsive gel contains therein, provided that the relationships explained above are satisfied. Where the stimulus-responsive gel comprising the optically active molecules is 100% by weight when it is dried, the concentration of the molecules is preferably in a range of 0.00001% or more by weight but 10% or less by weight, especially preferably in a range of 0.01% or more by weight but 10% or less by weight, and most preferably in a range of 0.1% or more by weight but 5% or less by weight. If the concentration of the molecules having the fluorescence chromophores or the molecules capable of absorbing the visible light or the ultraviolet light is greater than 0.00001% by weight, it is possible to appropriately convert the volume change into the optical data, referring to the proportional relationship between the fluorescence intensity or the absorbance, and the concentration of the molecule. Moreover, if the concentration of the molecules having the fluorescence chromophores or the molecules capable of absorbing the visible light or the ultraviolet light is less than 10% by weight, it is possible to appropriately convert the volume change into the optical data, referring to the proportional relationship between the fluorescence intensity or the absorbance, and the concentration of the molecule. It is preferable that the stimulus-responsive gel of the present invention have a smaller concentration of the molecules having the fluorescent group or absorbing the visible light or the ultraviolet light. This is because the conversion of the volume change into the optical change attained with a small amount of the molecules having the fluorescent group or absorbing the visible light or the ultraviolet light, and the addition of such a small amount of molecules into the gel will not change properties of the gel so much. Because of this, the concentration of the molecules having the fluorescent group or absorbing the visible light or the ultraviolet light is preferably 10% by weight or less in the stimulus-responsive gel of the present invention where the stimulus-responsive gel is 100% by weight when it is dried.

In the stimulus-responsive gel of the present invention, the molecules having the fluorescent group or absorbing the visible light or the ultraviolet light is introduced. Here, the molecules "introduced" are in such a state that the molecules having the fluorescent group or absorbing the visible light or the ultraviolet light are held in the stimulus-responsive gel of the present invention so that the molecules will not be discharged out of the stimulus-responsive gel together with the liquid when the stimulus-responsive gel changes its volume by absorbing or discharging the liquid in response to the external stimulus.

In order to attain the state that the molecules having the fluorescent group or absorbing the visible light or the ultraviolet light are held in the stimulus-responsive gel of the present invention so that the molecules will not be discharged out of the stimulus-responsive gel together with the liquid when the stimulus-responsive gel changes its volume by absorbing or discharging the liquid in response to the external stimulus. It is preferable for the stimulus-responsive gel of the present invention that the molecules having the fluorescent group or absorbing the visible light or the ultraviolet light is held in the stimulus-responsive gel via chemical bonding such as ionic bonding, covalent bonding, or the like. Moreover, in order that the molecules having the fluorescent group or absorbing the visible light or the ultraviolet light may not be discharged out of the stimulus-responsive gel, the molecules may be held via hydrogen bonding or electrostatic interaction, or may be held physically via a cross-linked network structure.

The stimulus-responsive gel of the present invention is not limited particularly as to the fluorescence chromophores, and may have any fluorescence chromophores. Examples of the fluorescence chromophores encompass anthracene, rhodamine, fluorescein, eosin, coumarin, erythrosine, acridine, pyrene, stilbene, naphthalene, nitrobenzoxazole, quinoline, azidoacridine, carbazole, pyridinium, and derivatives thereof.

The stimulus-responsive gel of the present invention is not limited particularly as to the molecules capable of absorbing the visible light and various dyes and pigments may be adopted in the present invention. Examples of the molecule capable of absorbing the visible light encompass azo dyes such as methyl yellow, methyl orange, methyl red, and the like, and cyanine dyes such as anthocyanin, phthalocyanine, and the like.

The stimulus-responsive gel of the present invention is not limited particularly as to the molecules capable of absorbing the ultraviolet light. Examples of the molecule capable of absorbing the ultraviolet light encompass anthracene, melanin pigment, flavone, benzophenone, nucleic acid, protein, and the like.

A polymer constituting the stimulus-responsive gel of the present invention may be any polymer, provided that the polymer allows the stimulus-responsive gel to change its volume by swelling or shrinking in response to the external stimulus such as pH, ionic concentration, heat, electricity, a recognizable molecule, a signal indicative of a change in a state of a living body, magnetic field, light, or the like. Specific examples of the stimulus-responsive gel which changes its volume in response to pH or ionic concentration encompass poly(meth)acrylic acid, polymaleic acid, polyvinylsulfonic acid, polyvinylbenzene sulfonate, polyacrylamidealkyl sulfonate, polyacrylamidealkyl sulfonate, polydimethylaminopropyl(meth)acrylamide, copolymers of them with (meth) acrylamide, hydroxyethyl(meth)acrylate or (meth)acrylic acid alkylester, and the like; a complex of polydimethylaminopropyl(meth)acrylamide and polyvinylalcohol; a complex of polyvinylalcohol and poly(meth)acrylate; metallic salts of carboxyalkylcellulose; poly(meth)acrylic nitrile, alginic acid, chitosan, metallic salts and cross-linked polymers thereof. Among them, the stimulus-responsive gel which changes its volume in response to pH or ionic concentration is preferably poly(meth)acrylate, a copolymer of (meth)acrylate with (meth) acrylamide, hydroxyethyl(meth)acrylate or (meth)acrylic acid alkylester, or the like, or a metallic salt or a cross-linked polymer thereof. In this DESCRIPTION, the term "(meth)acryl" means both "acryl" and "methacryl".

Specific examples of the stimulus-responsive gel, which changes its volume in response to heat, encompass polyalkyl-substituted (meth)acrylamides acrylamides (such as poly N-isopropyl(meth)acrylamide and the like), polyvinylmethylether, alkyl-substituted celluloses and derivatives thereof (such as methylcellulose, ethylcellulose, hydroxypropylcellulose), poly N-vinyl isobutylamide, copolymer of polyethyleneoxide with polypropyleneoxide, and cross-linked polymers thereof.

There is no particular limitation as to the stimulus-responsive gel, which changes its volume in response to the recognizable molecule. Examples of the stimulus-responsive gel encompass gels on which a recognizing material such as enzyme, antigen, antibody, nucleic acid, or the like is immobilized, the gels changing their volume in response to the pH, ionic concentration, heat, or the other stimulus. Moreover, the stimulus-responsive gel may be a gel on which a shape of the recognizable molecule is imprinted, the gel changing their volume in response to the pH, ionic concentration, heat, or the other stimulus.

Moreover, the stimulus-responsive gel, which changes its volume in response to electricity, is not particularly limited. Examples of such a stimulus-responsive gel encompass the stimulus-responsive gels mentioned above as the gels which change their volumes in response to pH or ionic concentration.

In general, a stimulus-responsive gel changes its volume by swelling or shrinking by absorbing or discharging a liquid in response to an external stimulus. The liquid that is absorbed in or discharged out of the stimulus-responsive gel is not particularly limited and may be water, an aqueous buffer solution, or an organic solvent. Specific examples of the liquid encompass: water; aqueous buffer solution such as phosphate buffer solution and the like; alcohols such as methanol, ethanol, 1-propanol, 2-propanol, 1-butanol, 2-butanol, isobutylalcohol, isopentylalcohol, and the like; ketones such as acetone, 2-butanon, 3-pentanon, methylisopropylketone, methyl n-propylketone, 3-hexanon, methdyl n-butyl ketone; ethers such as dimethylether, diisopropylether, tetrahydrofrane, tetrahydropyrane, etc.; esters such as acetic ethyl ester and the like; amides such as dimethylformamine, dimethylacetoaminde and the like; dimethylsulfoxide; nitriles such as acetonitorile; propylene carbonate; lower saturated carbohydrate such as pentane, hexane, cyclohexane, and the like; xylene; toluene; and a mixture of two or more of them; and the like.

The stimulus-responsive gel of the present invention is not particularly limited in terms of its shape and may have any shape. The stimulus-responsive gel of the present invention may have a shape preferable for the usage as appropriate. Examples of the shape encompass a circular cylinder shape, sheet shape, film shape, particle shapes, rectangular shape, etc. For example, in case where an apparatus such as a fluorescent spectrometer is used, or in case where the optically active molecule-introduced stimulus-responsive gel is used in a gel chip for use in a diagnosis system, the sheet shape and the film shape are preferable.

Shaping the stimulus-responsive gel into a desired shape may be carried out by introducing raw materials of the stimulus-responsive gel, such as the monomer constituent and the like, into a mold of the desired shape before polymerization, and then performing the polymerization.

The stimulus-responsive gel is not particularly limited in terms of its size and may be in any size. The stimulus-responsive gel may have a size preferable for its usage.

(I-2) Method of Producing the Stimulus-Responsive Gel of Present Invention

The stimulus-responsive gel of the present invention with optically active molecules introduced therein is produced in such a manner that the optically active molecules (molecules having the fluorescence chromophores or the molecules capable of absorbing the visible light or ultraviolet light) are held in the stimulus-responsive gel via e.g. chemical bonding so that the optically active molecule will not be discharged together with the liquid when the stimulus-responsive gel changes its volume in response to the external stimulus by absorbing or discharging the liquid, as described above. One example of the method is to perform the polymerization of the stimulus-responsive gel by adding a molecule having a polymerizing group and the fluorescence chromophore, or a molecule having a polymerizing group and absorbing the visible light or the ultraviolet light to a monomer constituting the main chain of the stimulus-responsive gel. That is, the stimulus-responsive gel of the present invention can be easily produced by polymerizing the monomer with the molecule by applying heat, light, or the like externally, with or without using a solvent. In case where the solvent is used, the stimulus-responsive gel of the present invention can be easily produced by dissolving in an appropriate solvent (a) a molecule having a polymerizing group and the fluorescence chromophore, or a molecule having a polymerizing group and absorbing the visible light or the ultraviolet light, (b) a monomer constituting the main chain of the stimulus-responsive gel, (c) an initiating agent, (d) a cross-linking agent, (e) and the like, and then polymerizing the monomer with the molecule by applying heat, light, or the like externally.

In order to produce the stimulus-responsive gel that changes its volume in response to the recognizable molecule, the polymerization is carried out by further adding a polymerizing group-introduced recognizing material such as an enzyme, antigen, antibody, nucleic acid, or the like. In order to produce the stimulus-responsive gel which is imprinted in the shape of the recognizable molecule, the polymerization is carried out by adding the recognizable molecule and a polymerizing group-introduced ligand specifically bondable with the recognizable molecule, and then removing the recognizable molecule from the obtained polymer. The recognizable molecule and the polymerizing group-introduced ligand may be added together or added after forming a clathrate with the polymerizing group-introduced ligand trapping the recognizable molecule therein.

Needless to say, the polymerizing group in the polymerizing group-introduced molecule having the fluorescent group, polymerizing group-introduced enzyme, antigen, antibody, nucleic acid, etc. and polymerizing group-introduced ligand may be replaced with a reactive functional group other than the polymerizing group. Any group may be adopted as the reactive functional group provided that the group is chemically bondable with the polymer compound that forms the network structure of the polymer gel. Examples of the group encompass vinyl group, (meth)acryloyl group, hydrate group, carboxylic group, amino group, and the like.

The monomer may be any monomer, provided that it constitutes the main chain of the polymer constituting the stimulus-responsive gel. Specific examples of the monomer encompass: (meth)acrylic acid, maleic acid, vinylsulfonate, vinylbenzene sulfonate, acrylamidealkylsulfonate, acrylamidealkylsulfonate, amino-substituted (meth)acrylamides (such as dimethylaminopropyl(meth)acrylamide), (meth) acrylic nitril, vinylsulfonate, vinylbenzensulfonate, dimethylaminopropyl(meth)acrylamide, dimethylaminoethyl(meth) acrylate, diethylaminoethyl(meth)acrylate, amino (meth) acrylate-substituted alkylesters (such as dimethylaminopropyl(meth)acrylate), styrene, vinylpyridine, vinylcarbazole, dimethylaminostyrene, alkyl-substituted (meth)acryl amides (such as N-isopropyl(meth)acryl amide), and the like compounds. They may be used solely or two or more of them may be used in combination.

The cross-linking agent is not particularly limited. Specific examples of the cross-linking agent encompass: ethyleneglycol di(meth)acrylate, propyleneglycol di(meth)acrylate, N,N'-methylenebisacryl amide, tolylenediisocyanate, divinylbenzene, polyethyleneglycol di(meth)acrylate, and the like.

Moreover, the polymerization initiating agent is not particularly limited. Preferable examples encompass: persulfates such as ammonium persulfate, sodium persulfate, ammonium persulfate, and the like; hydrogen peroxide; peroxides such as t-butylhydroperooxide, cumenehydroperoxide, and the like; azobisiobutyronitrile; benzoyl peroxide, etc. Among these polymerization initiating agents, especially, acidic initiating agents such as persulfates, peroxides, and the like can be used a redox initiating agents, for example with sodium hydrogen sulfite, N,N,N',N'-tetramethylethylenediamine, or the like.

The method of producing the stimulus-responsive gel in which the molecule having the fluorescence chromophore or absorbing the visible light or the ultraviolet light is introduced via the chemical bonding is not limited to the method explained above. The molecule having the fluorescence chromophore or absorbing the visible light or the ultraviolet light may be introduced via the chemical bonding to the stimulus-responsive gel after the polymerization of the monomer to form the main chain of the stimulus-responsive gel. For example, this may be carried out by bonding a polymer (polyvinyl alcohol, cellulose, polyacrylic acid, or the like) having a reactive functional group (such a hydroxyl group, carboxyl group, or the like) or such a polymer cross-linked, and a molecule having a reactive functional group and the fluorescence chromophore or a molecule having a functional group and absorbing the visible light or the ultraviolet light via reaction between the functional group (polymerization) thereby to obtain the targeted stimulus-responsive gel.

Moreover, the stimulus-responsive gel may be produced by physically holding with a cross-linked network structure the molecules having the fluorescence chromophores or the molecules capable of absorbing the visible light or the ultraviolet light, so that the molecules will not be discharged out of the stimulus-responsive gel. This may be carried out by mixing and evenly dispersing the molecules having the fluorescence chromophores or the molecules capable of absorbing the visible light or the ultraviolet light in the polymer formed from the monomer constituent of the stimulus-responsive gel, and then performing cross-linking, etc. The even dispersion of the molecules having the fluorescence chromophores or the molecules capable of absorbing the visible light or the ultraviolet light can be done by mechanically mixing and kneading, by using a dispersing agent, or by the other method.

(II) External Stimulus Measuring Apparatus

With the stimulus-responsive gel of the present invention, the volume change in the stimulus-responsive gel by and according to the external stimulus can be converted into the optical data in the form of the change in the fluorescence intensity or the absorbance. Thus, the stimulus-responsive gel can be used as a sensor element in a simple system. This eliminates the need of measuring the volume by a microscopy or the like, or measuring the weight by a scale or the like. The stimulus-responsive gel can quantitatively express the volume change thereby quantitatively showing the optical measurements in fluorescence intensity or the absorbance. Thus, the present invention encompasses an external stimulus measuring apparatus for converting into the optical data the volume change in the stimulus-responsive gel in response to the external stimulus and detecting or measuring the external stimulus from the optical data.

There linear relationship in plotting the logarithms of the volume change against the logarithms of the fluorescence intensity or the absorbance is explained as follows.

In general, the fluorescence intensity F and the concentration C of the fluorescent molecules have a relationship as expressed by Equation (1) when the concentration of the fluorescent molecules in a solution is low:

$$F \propto \epsilon Cl \quad (1)$$

where $\epsilon$ is absorbance coefficient of the fluorescent molecules and l is a length of a sample to be measured. Therefore, when the relationship between concentration of the fluorescence chromophores in the gel and the fluorescence intensity is applied to a control solution having no external stimulus and a stimulus solution in which an external stimulus, e.g., ionic concentration or the like, is given, Equation (2) is obtained:

$$\frac{F}{F_0} = \frac{Cl}{C_0 l_0} \quad (2)$$

where the reference numerals with subscripted O are values of the control solution and the reference numerals without subscripted O are values of the stimulus solution. The absolute quantity n of the fluorescence chromophore in the gel is constant when the volume V of the gel is changed in the control solution and the stimulus solution. Thus, there is a relationship as follows:

$$C = \frac{n}{V} \propto \frac{n}{l^3} \quad (3)$$

$$C_0 = \frac{n}{V_0} \propto \frac{n}{l_0^3} \quad (4)$$

Meanwhile, the swelling ratio Q is defined as Equation (5) and has a relationship with l as below.

$$Q = V/V_0 \quad (5)$$

$$Q = \left(\frac{l}{l_0}\right)^3 \quad (6)$$

Substituting with Equations (3), (4) and (6), Equation (2) can be expressed as follows to show the relationship between the swelling ratios and fluorescence intensity of the gels.

$$\frac{F}{F_0} = Q^{-\frac{2}{3}} \quad (7)$$

$$\log\left(\frac{F}{F_0}\right) = -\frac{2}{3}\log Q \quad (8)$$

Figure 5:
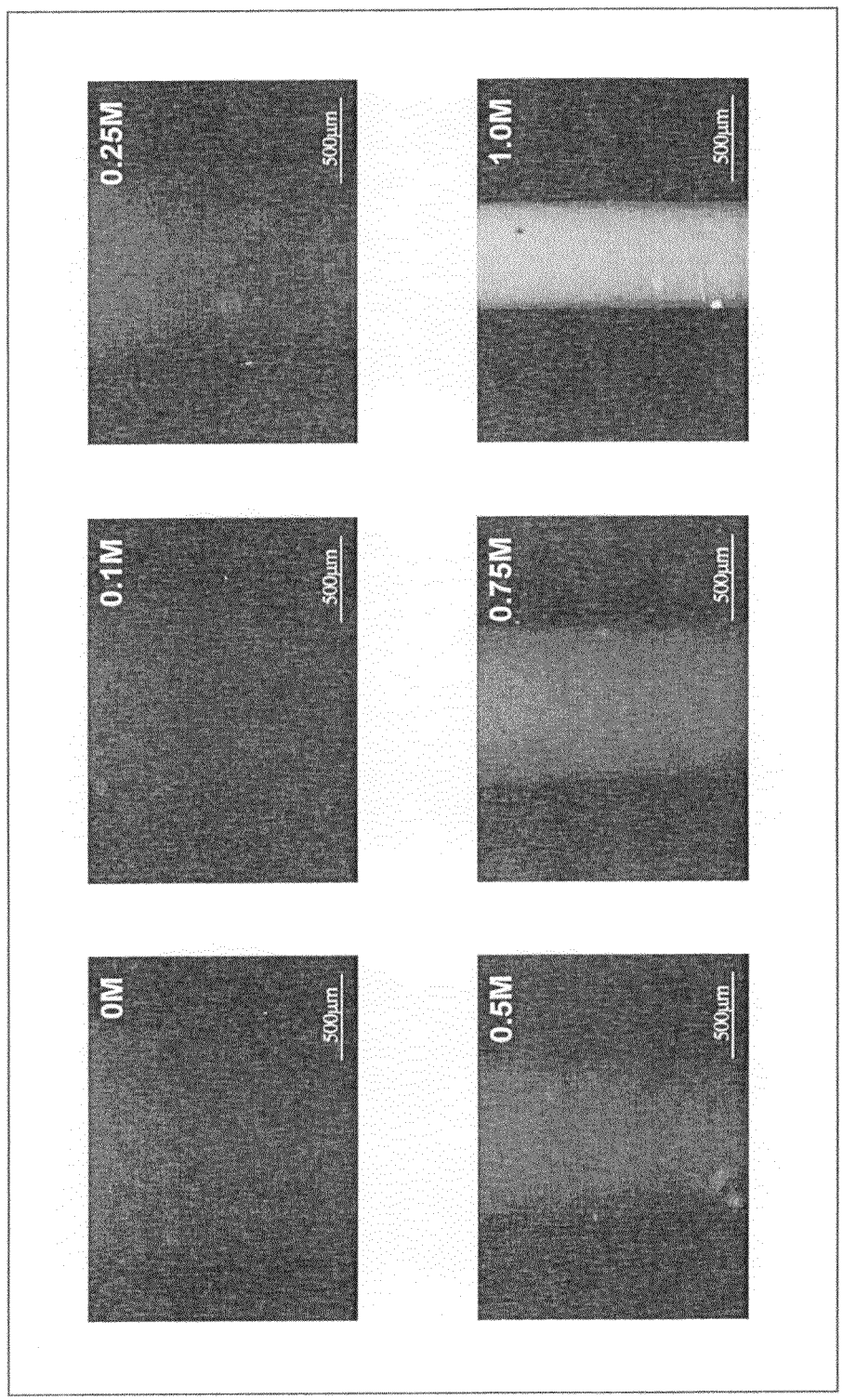
FIG. 5 is a view illustrating a relationship between the swelling ratios (volume change) of cylinder-shaped PAAc-EDANS gel and fluorescence intensity in Examples.
Figure 6:
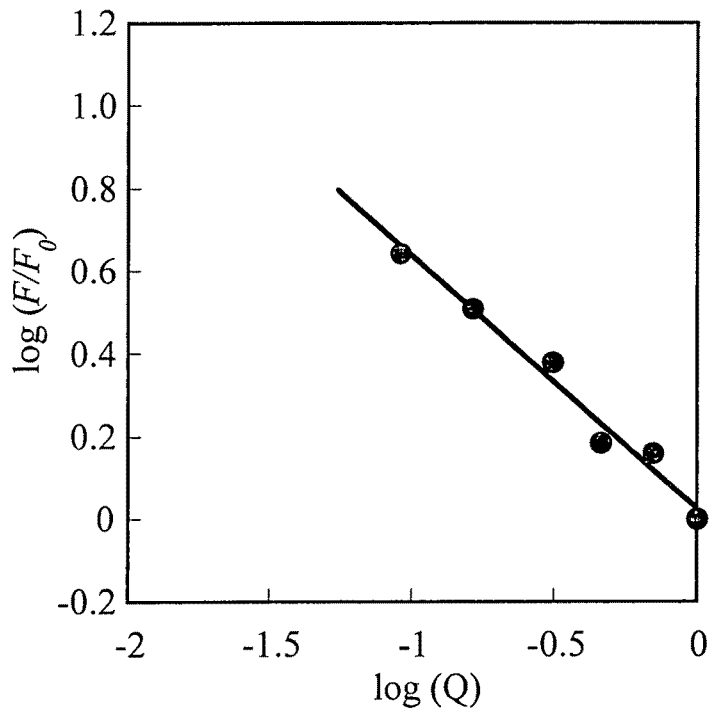
FIG. 6 is a graph plotting relative fluorescence intensity against the swelling ratio (volume change) of cylinder-shaped PAAc-EDANS gel in Examples.

As a result, logarithms of the swelling ratio are plotted against logarithms of the fluorescence intensity showing a strain line with a gradient of −⅔. This result matches well with the straight line with the gradient of −0.65, the straight line being obtained from FIGS. 5 and 6 showing a relationship between the logarithms of a swelling ratio and fluorescence intensity of the PAAc-EDANS gel measured in the later-described Example.

It is expected that a similar relationship exists between a swelling ratio and absorbance of the ultraviolet light or the visible light in the gel in which the molecules capable of absorbing the ultraviolet light or the visible light are introduced. That is, according to the Lambert-Beer's law (Equation 9), which is a general theory regarding ultra violet absorbance and a visible light absorbance, the relationship exists between a swelling ratio and absorbance in the gel can be expressed as Equation (10), showing that a relative absorbance is proportional with the power of −⅔ of the swelling ratio.

$$A = \varepsilon C l \quad (9)$$

$$\frac{A}{A_0} = Q^{-\frac{2}{3}} \text{ or } \log(A/A_0) = -\frac{2}{3}[\log Q] \quad (10)$$

The external stimulus measuring apparatus of the present invention comprises at least (a) a sample section including the stimulus-responsive gel of the present invention and a liquid, which is absorbed in or discharged out of the stimulus-responsive gel in response to the external stimulus, and (b) an optical data measuring section for irradiating the light of a particular wavelength on the sample section and measuring the fluorescence intensity or the absorbance of the visible light or the ultraviolet light therein. The stimulus-responsive gel, the external stimulus, and the liquid are explained in Item (I-1) Stimulus-responsive gel of Present Invention. Thus, their explanation is omitted here.

Figure 9:
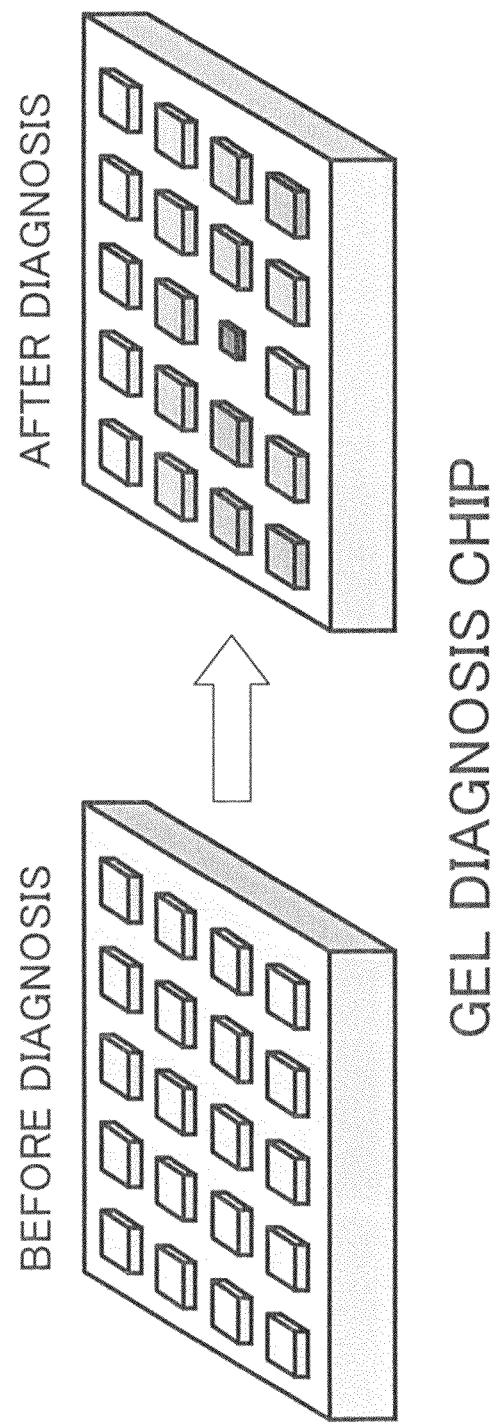
FIG. 9 is a view illustrating a configuration in which gel chips are arrayed, the gel chips being formed from the stimulus-responsive gel of the present invention with optically active molecules introduced therein.

The sample section at least comprises the stimulus-responsive gel of the present invention and the liquid, which is absorbed in or discharged out of the stimulus-responsive gel in response to the an external stimulus. The liquid is in contact with the stimulus-responsive gel in such a manner that the liquid is freely absorbed in or discharged out of the stimulus-responsive gel. At the sample section, the stimulus-responsive gel is exposed to an external stimulus such as pH, ionic concentration, heat, electricity, recognizable molecule, magnetic field, light, or the like, and changes its volume by absorbing or discharging the liquid in coexistence therewith in response to the external stimulus. Therefore, in the case where the external stimulus is pH, ionic concentration, recognizable molecule, or the like, the sample section should be arranged such that the stimulus-responsive gel can be in contact with a solution or a molecule, which gives the external stimulus. Moreover, in case where the external stimulus is heat, electricity, or the like, the stimulus-responsive gel does not need to be in direct contact with the external stimulus. Thus, the sample section may be a closed system. Moreover, a sample in the sample section may be in any size or number according to a purpose. For example, in order to perform plural measurements at once, gel chips may be arranged in array as illustrated in FIG. 9.

Moreover, the optical data measuring section should be able to irradiate the light of the particular wavelength to the sample section and measure the fluorescence intensity, or the absorbance of the visible light or the ultraviolet light. In the case where the stimulus-responsive gel used in the external stimulus measuring apparatus of the present invention is a gel in which the molecules having the fluorescence chromophores are introduced, the intensity of the fluorescent light emitted by the irradiation of exiting light onto the sample section is measured. There is no particular limitation as to a measuring method of the fluorescence intensity. A suitable measuring method may be selected according to the shape of the stimulus-responsive gel or the like conditions. The fluorescence intensity may be measured by, for example, using a fluorescent spectrometer, by image analysis via fluorescent microscopic observation, or by the like method. The image analysis to measure the fluorescence intensity is not particularly limited and may be carried out by a method including reading a fluorescent microscopic image in a computer, converting the fluorescent microscopic image into a gray scale image via image analysis software, indicating brightness of the image as a histogram, and then calculating relative fluorescence intensity from the values of the histogram, or the like method. Moreover, the image analysis software is not particularly limited, provided that the image analysis software can convert the image into a histogram.

In the case where the stimulus-responsive gel used in the external stimulus measuring method of the present invention is a gel in which the molecules capable of absorbing the visible light or the ultraviolet light are introduced, the absorbance of reflective light or transparent light resulted from the irradiation of the particular wavelength that the introduced light absorbs is measured. In the measured. In the case where the stimulus-responsive gel used in the external stimulus measuring method of the present invention is a gel in which the molecules capable of absorbing the visible light are introduced, the degree of the absorbance can be confirmed visually.

The external stimulus measuring apparatus of the present invention is preferably arranged such that it further comprises an optical data outputting section for converting into an electric signal the fluorescent intensity or the absorbance of the visible light or the ultraviolet light measured by the optical data measuring section, and outputting the electric signal. With this arrangement, it becomes easier to obtain the external-stimulus caused volume change of the stimulus-responsive gel in the form of the electric signal, which is easy to process as data and makes it possible to automate the measurement.

The external stimulus measuring apparatus of the present invention may comprise a computing section for calculating out, from the electric signal outputted from the optical data outputting section, how large the external stimulus causing the volume change in the stimulus-responsive gel is. The computing section is preferably arranged such that it stores an analytical curve that indicates the degree of the external stimulus from the fluorescence intensity or the absorbance of the visible light or the ultraviolet light. The analytical curve indicates correlation between the fluorescence intensity, absorbance, or the like and the volume change of the stimulus-responsive gel. The analytical curve is determined in advance by obtaining the optical data such as the fluorescence intensity, absorbance, or the like, which is converted from the volume change of the stimulus-responsive gel, the volume change being caused by and according to the external stimulus. By storing the analytical curve, it becomes possible to detect and measure the degree of the external stimulus automatically from the obtained optical data. Moreover, the external stimulus measuring apparatus of the present invention is not limited to the purpose of detecting and measuring the degree of the external stimulus, and is very effective to judging whether the external stimulus is greater or less than a certain level thereof which corresponds to a value of the optical data stored.

(III) Method of Measuring External Stimulus

With the stimulus-responsive gel of the present invention, the volume change in the stimulus-responsive gel by and according to the external stimulus can be converted into the optical data as the change in the fluorescence intensity or the absorbance. Thus, the stimulus-responsive gel can be used as a sensor element in a simple system. Thus, the present invention encompasses a method of measuring the external stimulus, the method comprising converting into the optical data the volume change in the stimulus-responsive gel in response to the external stimulus and detecting or measuring the external stimulus from the optical data.

The method of the present invention for measuring the external stimulus comprises: (a) determining an analytical curve by (i) exposing to external stimuli of different known degrees the stimulus-responsive gel of the present invention in the presence of a liquid, which is absorbed in or discharged out of the stimulus-responsive gel in response to the external stimulus, so as to cause the volume changes in the stimulus-responsive gel, (ii) irradiating the light of a particular wavelength on the stimulus-responsive gel exposed to the respective external stimuli of different degrees, and (iii) measuring the fluorescence intensity or the absorbance of the visible light or the ultraviolet light therein; (b) (i) exposing to an external stimulus of an unknown degree the stimulus-responsive gel of the present invention in the presence of the liquid, (ii) irradiating the light of the particular wavelength on the stimulus-responsive gel exposed to the external stimulus of the unknown degree, and (iii) measuring the fluorescence intensity or the absorbance of the visible light or the ultraviolet light in the stimulus-responsive gel; and (c) determining how large the external stimulus of the unknown degree is, from the measured fluorescence intensity or the absorbance of the visible light or ultraviolet light by using the analytical curve.

EXAMPLES

In the following, the present invention is described in more details via Examples, which are not to limit the present invention.

Example 1

Production of Optically Active Molecule-Introduced Stimulus-Responsive Gel

<Synthesis of Vinyl Group-Introduced 5-(2'-aminoethyl)aminonaphthalene-1-sulfonate (EDANS)>

As illustrated in FIG. 1, a vinyl group was introduced in EDANS. Into the EDANS of 50 mg (0.18 mmol), sodium hydrogen carbonate of 420 mg (5.00 mmol), and N-succinimidylacrylate (NSA) of 38 mg (0.22 mmol), pure water of 25 ml was added. Then, the mixture was stirred overnight. Then, concentrated hydrochloric acid was added therein to weakly acidify the mixture. After that, acetone was added to the mixture thereby precipitating inorganic salts such as sodium hydrogen carbonate and the like. Then, a filtrate obtained by filtering the mixture was concentrated and then fractioned via a silica gel chromatography (Wakogel C-200, Wako Pure Chemical Industries, Ltd.), thereby obtaining a fraction. The fraction was concentrated, washed with ethyl acetate, and then dried at room temperatures under vacuum. Thereby, vinyl group introduced EDANS (vinyl-EDANS) was obtained.

<Synthesis of Optically Active Molecule-Introduced Stimulus-Responsive Gel in which Fluorescence Chromophore (PAAc-EDANS gel)>

Figure 2:
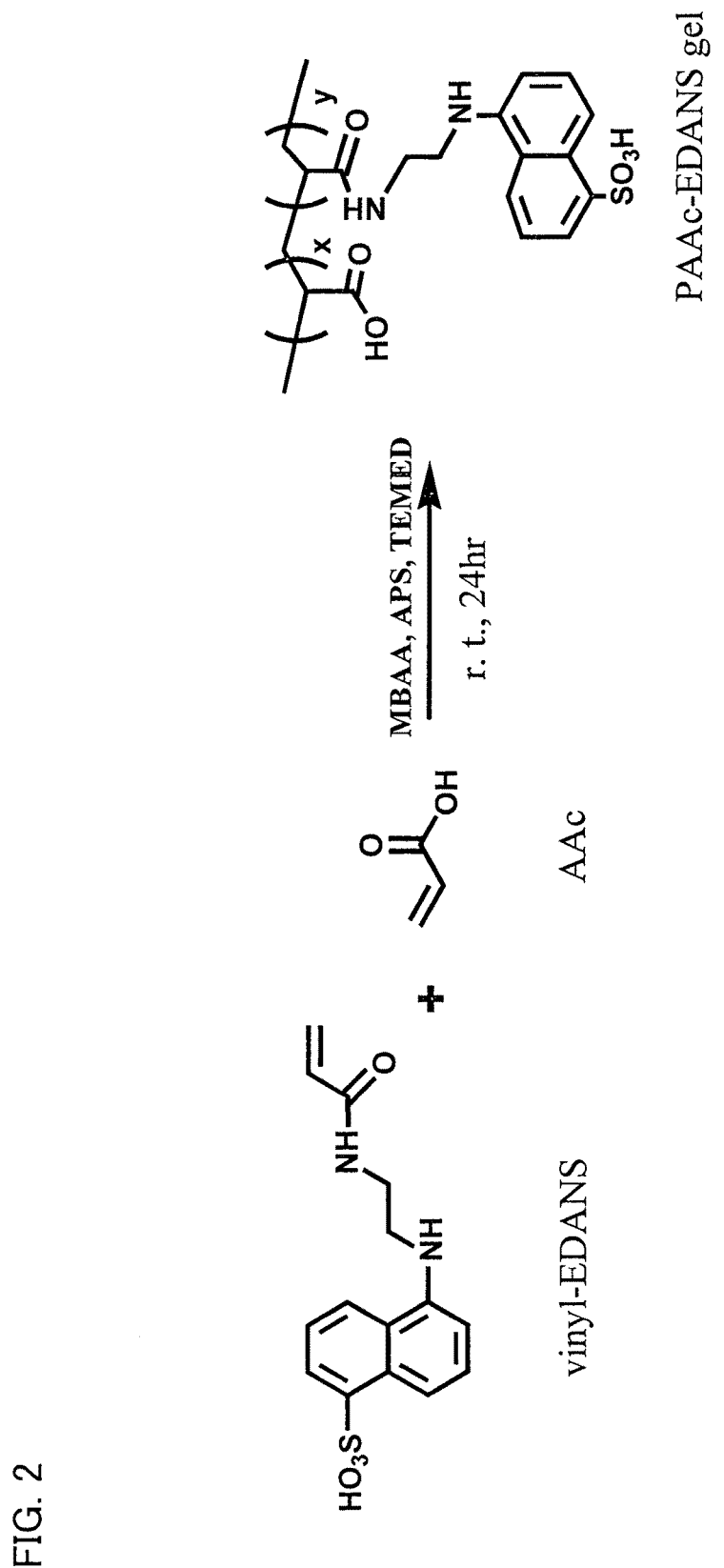
FIG. 2 is a view illustrating a chemical reaction formula for producing a stimulus-responsive gel with optically active molecule introduced therein (PAAc-EDANS gel) in which a fluorescent chromophore is introduced, in Examples.

An optically active molecule-introduced stimulus-responsive gel (PAAc-EDANS gel) in which a fluorescence chromophore was introduced was synthesized in the way illustrated in the chemical reaction formula in FIG. 2. Added into 7.613 g of pure water were 2 g of acrylic acid (AAc), 0.087 ml of vinyl-EDANS of a concentration of 100 mg/ml, 0.1 ml of N,N'-methylenebisacrylamide (MBAA) of a concentration of 20 mg/ml, and a redox initiating agent (0.1 ml of 0.1M ammonium persulfate (APS), and 0.1 ml of 0.8M N,N,N',N'-tetramethylethylenediamine (TEMED)). The mixture thus obtained was purred into a glass tube of 0.7 mm internal diameter and a gap between glass plates with a silicon spacer of 1 mm thickness therebetween. Then, polymerization was carried out for 24 hours at 25° C., thereby synthesizing PAAc-EDANS gel in a cylinder shape and a sheet shape.

Example 2

Measurement of Volume Change in Optically Active Molecule-Introduced Stimulus-Responsive Gel in Cylinder Shape The optically active molecule-introduced stimulus-responsive gel (PAAc-EDANS gel) in the cylinder shape produced in Example 1 was sufficiently swollen to equilibrium in pure water, and then shrunk to equilibrium in sodium chloride (NaCl) aqueous solutions of various concentrations. The Volume change in the PAAc-EDANS gel was worked out as the swelling ratio (volume change) expressed in Equation (11) below by measuring the changes in the diameters of the gels in the NaCl aqueous solutions of various concentrations.

Swelling Ratio (Volume Change)=$(d/d0)_3$ ... (11), where d0 is the diameter (cm) of the PAAc-EDANS gel of the cylinder shape in pure water, and d is the diameter (cm) of the PAAc-EDANS gel of the cylinder shape in the NaCl aqueous solutions.

Figure 3:
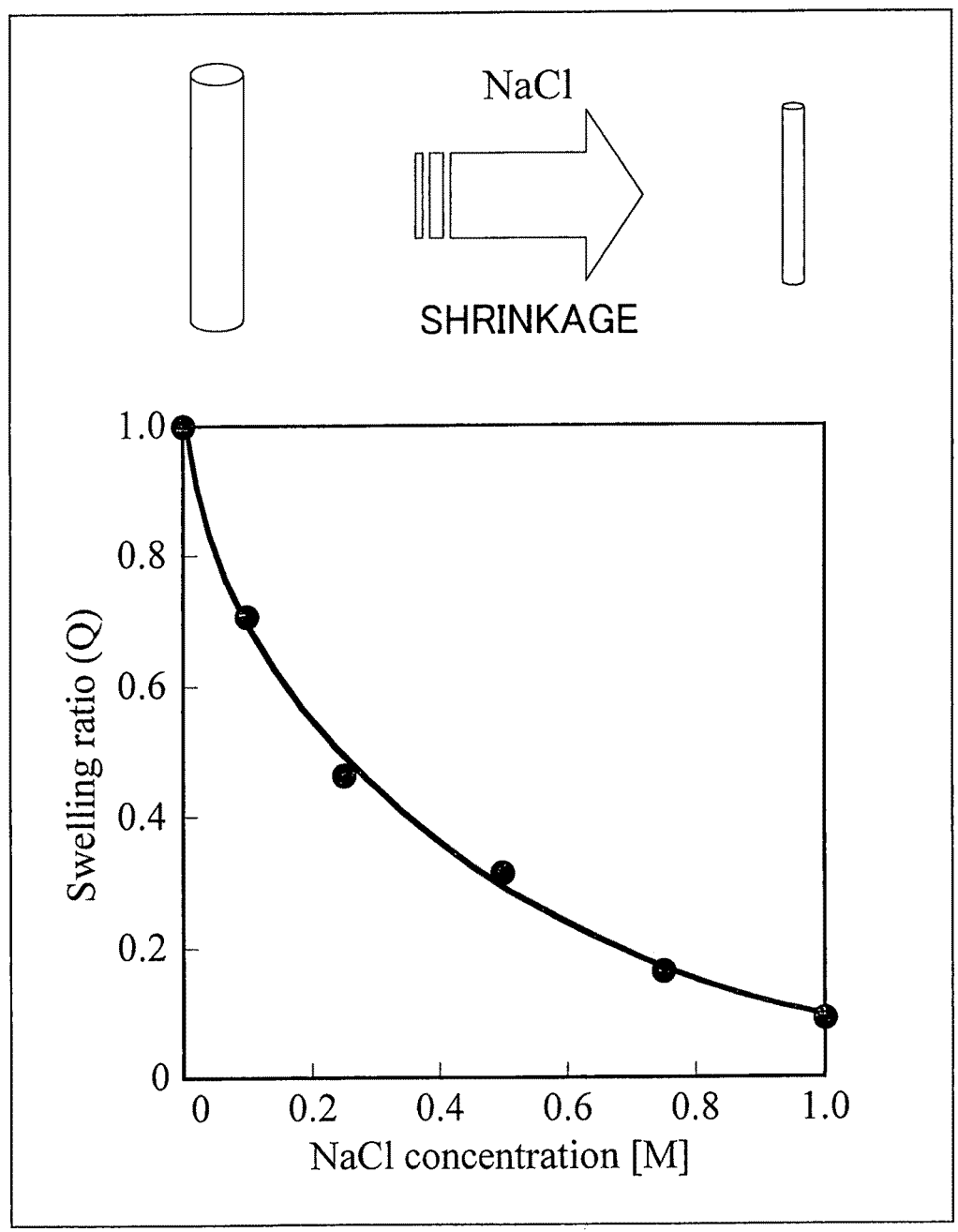
FIG. 3 is a graph illustrating swelling ratios (volume change) of cylinder-shaped PAAc-EDANS gel in NaCl aqueous solutions of various densities in Examples.

FIG. 3 illustrates the swelling ratio (volume change) of the PAAc-EDANS gel of the cylinder shape in the NaCl aqueous solutions of various concentrations. In FIG. 3, the vertical axis indicates the swelling ratio (volume change), and the horizontal axis is the mol concentration of the NaCl aqueous solutions. As illustrated in FIG. 3, the swelling ratio of the PAAc-EDANS gel was reduced gradually as the mol concentration of NaCl was increased. It is deduced that this phenomenon occurred because the electric charge on —COO— in the network of the PAAc-EDANS gel was shielded as the ionic strength was increased.

Example 3

Measurement of Swelling Ratio (Weight Change) in the Optically Active Molecule-Introduced Stimulus-Responsive Gel of Sheet Shape The optically active molecule-introduced stimulus-responsive gel (PAAc-EDANS gel) in the sheet shape produced in Example 1 was sufficiently swollen to equilibrium in pure water, and then shrunk to equilibrium in sodium chloride (NaCl) aqueous solutions of various concentrations. The weight change in the PAAc-EDANS gel was worked out as the swelling ratio (weight change) expressed in Equation (12) below by measuring the changes in the weights of the gels in the NaCl aqueous solutions of various concentrations.

Swelling Ratio (Weight Change)=w/w0 ... (12), where w0 is the weight (g) of the PAAc-EDANS gel of the sheet shape in water, and w is the weights (g) of the PAAc-EDANS gel of the sheet shape in the NaCl aqueous solutions.

Figure 4:
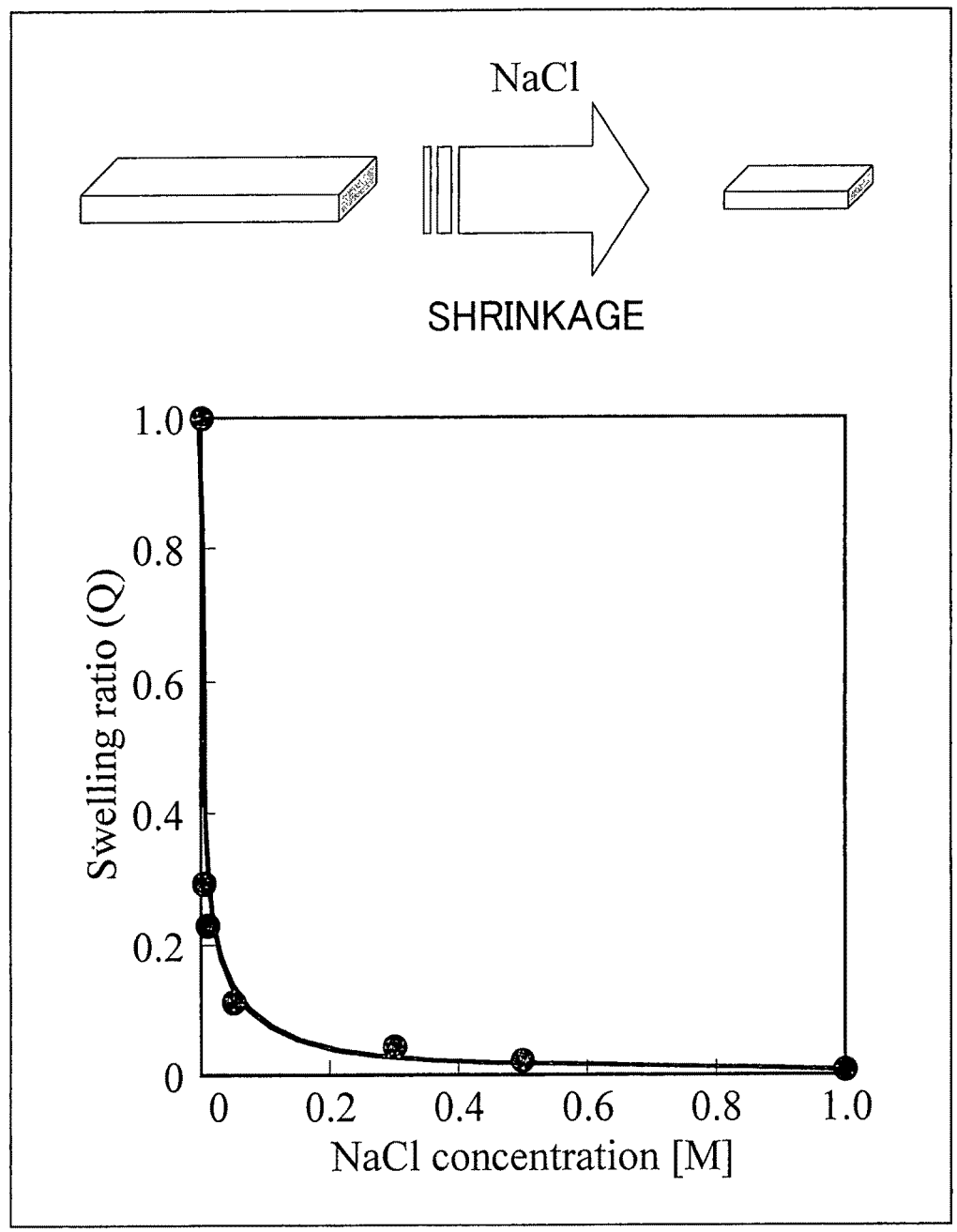
FIG. 4 is a graph illustrating swelling ratios (weight change) of sheet-shaped PAAc-EDANS gel in NaCl aqueous solutions of various densities in Examples.

FIG. 4 illustrates the swelling ratio (weight change) of the PAAc-EDANS gel of the sheet shape in the NaCl aqueous solutions of various concentrations. In FIG. 4, the vertical axis indicates the swelling ratio (weight change), and the horizontal axis is the mol concentration of the NaCl aqueous solutions. As illustrated in FIG. 4, the swelling ratio of the PAAc-EDANS gel was reduced gradually, again, as the mol concentration of NaCl was increased.

Example 4

Observation of Fluorescence Emitting Characteristic and Measurement of Fluorescence Intensity in Optically Active Molecule-Introduced Stimulus-Responsive Gel of Cylinder Shape Next, in order to study the relationship between the swelling ratio (volume change) and the fluorescence intensity of the gel, the PAAc-EDANS gel of the cylinder shape was immersed in various NaCl solutions and observed by fluorescent microscopic observation. The optically active molecule-introduced stimulus-responsive gels (PAAc-EDANS gel) in the cylinder shape and the sheet shape produced in Example 1 were sufficiently swollen to equilibrium in pure water, and then shrunk to equilibrium in sodium chloride (NaCl) aqueous solutions of various concentrations. The PAAc-EDANS gels of the cylinder shape in the respective concentrations were observed by fluorescent microscopic observation via an epifluorescent observing apparatus (fluorescent mirror unit U-MWU (excitation filter BP 330-385, dichroic mirror DM 400, absorption filter BA420); Olympus Corporation: IX-FLA) attached to an inverted microscope (Olympus Corporation: IX-70).

Figure 8:
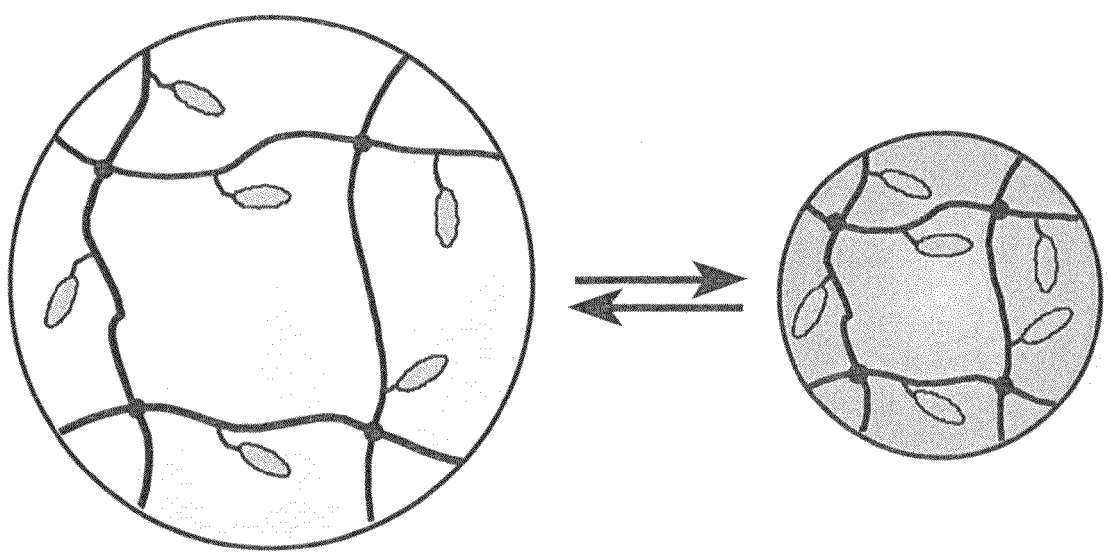
FIG. 8 is a view schematically illustrating the relationship between the fluorescence intensity and the swelling ratio of the stimulus-responsive gel of the present invention with optically active molecules introduced therein.

FIG. 5 illustrates the results of the fluorescent microscopic observation. FIG. 5 demonstrates that the fluorescence intensity of the PAAc-EDANS gel was increased in the fluorescent microscopic pictures when the PAAc-EDANS gel was shrunk due to the increase in the NaCl concentration of the surrounding solution. It is deduced that the increase in the fluorescence intensity associated with the shrinkage of the PAAc-EDANS gel was caused because the fluorescence chromophore, that is, EDANS (indicated by ellipsoids in FIG. 8) was increased in concentration as a result of a decrease in the volume of the PAAc-EDANS gel while the absolute amount of the fluorescence chromophore, that is, EDANS (indicated by ellipsoids in FIG. 8) was constant in the gel. Image analysis was performed on the fluorescent microscopic pictures in order to calculate out the relative fluorescence intensities thereby to find out the relationship between the swelling ratio (volume change) of the gel and the fluorescence intensity. The calculation of the fluorescence intensity was carried out as follows. The fluorescent microscopic picture was read into a computer and converted into a gray scale image via image analysis software (Origin Ver. 7.5). Then, brightness of the image was indicated as a histogram and then the relative fluorescence intensity was calculated from the values of the histogram.

FIG. 6 illustrates a relationship between a relative fluorescence intensity and the swelling ratio (volume change) of the PAAc-EDANS gel, the relationship being worked out by the image analysis of the fluorescent microscopic pictures illustrated in FIG. 5. In FIG. 6, the vertical axis indicates logarithms of the relative fluorescence intensity (F/F0), and the horizontal axis indicates logarithms of the swelling ratio (volume change). The relative fluorescence intensity is a ratio of the brightness (F) of the gel in the NaCl aqueous solutions over the brightness (F0) in the gel in the pure water, the brightness being obtained via the image analysis. As shown in FIG. 6, there is a linear relationship clearly between the logarithms of the swelling ratio (volume change) and the fluorescent intensity. The straight line had a gradient of −0.65. It was proved that the swelling ratio (volume change) of the PAAc-EDANS gel strongly correlates with the fluorescence intensity, and that the volume of the PAAc-EDANS gel can be data-converted into the fluorescence.

Example 5

Measurement of Fluorescence Intensity of Optically Active Molecule-Introduced Stimulus-Responsive Gel of Sheet Shape Next, the fluorescence intensity (at wavelength of 480 nm) of the sheet-shaped gel excited at wavelength of 340 nm was measured by using a fluorescent spectrometer (Shimadzu Corporation: RF-5300PC).

Figure 7:
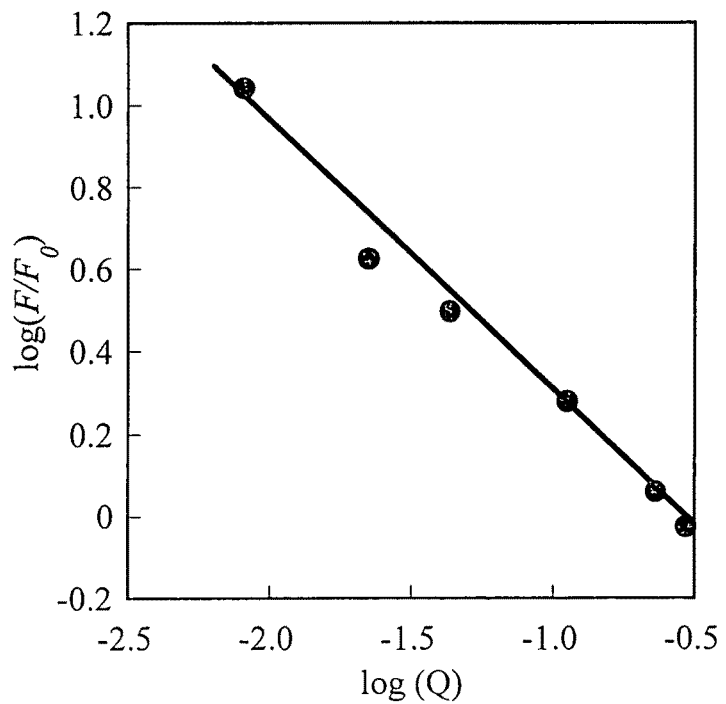
FIG. 7 is a graph plotting relative fluorescence intensity against the swelling ratio (weight change) of sheet-shaped PAAc-EDANS gel in Examples.

In order to study the influence of the shape of the gel on the relationship between the volume and the fluorescence intensity of the gel, the relationship between the swelling ratio (weight change) and the fluorescence intensity of the sheet-shaped gel was analyzed. FIG. 7 illustrates the relationship between the swelling ratio (weight change) and the relative fluorescence intensity of the sheet-shaped PAAc-EDANS gel. Here, because the gel had the sheet shape, the fluorescence intensity was directly measured by using the fluorescence spectrometer, and expressed as a ratio of the fluorescence intensity (F) of the gel in the NaCl aqueous solutions over the fluorescence intensity (F0) of the gel in pure water. In FIG. 7, the vertical axis indicates logarithms of the relative fluorescence intensity (F/F0), while the horizontal axis indicates the logarithms of the swelling ratio (volume change).

FIG. 7 shows that there is a clear linear relationship between the logarithms of the swelling ratio (weight change) and the fluorescence intensity. The straight light was sloped with a gradient of −0.65 as in the cylinder-shaped gel. This proves that the swelling ratio (weight change) approximated the swelling ratio (volume change) in the present Example, and therefore there is a clear correlation between the swelling ratio and the fluorescence intensity of the fluorescent chromophore-introduced gel regardless of the shapes of the gel and the fluorescence intensity was proportional with the −0.65 power of the swelling ratio.

Examples 6

Production of Optically Active Molecule-Introduced Stimulus-Responsive Gel that is Responsive to Bisphenol A In the present Example, bisphenol A (BPA), which was doubted as an endocrine disrupter (environmental hormone), was selected as a target molecule, and a stimulus-responsive gel (BPA-responsive gel) responsive to bisphenol A was synthesized, in which the fluorescence chromophore was introduced. The synthesis of the stimulus-responsive gel was carried out by adding a polymerizing group-introduced fluorescence chromophore in synthesizing the optically active molecule-introduced stimulus-responsive gel (BPA-responsive gel) by the molecular imprinting method using cyclodextrin as the ligand recognizing the bisphenol A.
<Synthesis of Acryloyl-6-Amino-6-Deoxy-β-Cyclodextrin (Acryloyl-CD)

Figure 10:
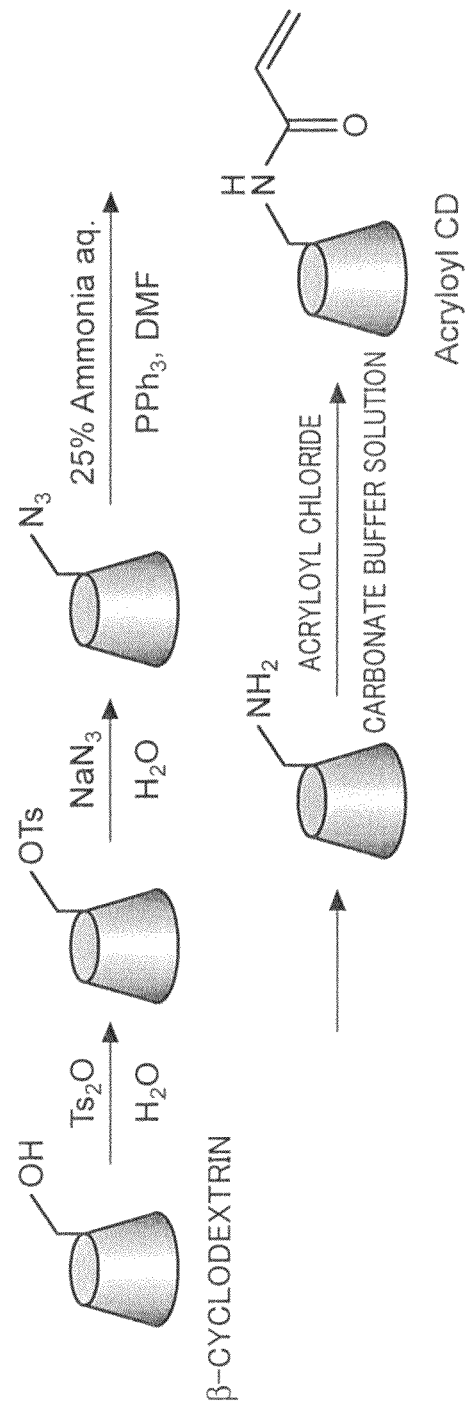
FIG. 10 is a view illustrating a scheme of synthesizing acryloyl-6-amino-6-deoxy-β-cyclodextrin for use in production of a stimulus-responsive gel with optically active molecules introduced therein (BPA-responsive gel with EDANS-introduced therein) in Example, the stimulus-responsive gel being responsive to bisphenol A.

First, acryloyl-6-amino-6-deoxy-β-cyclodextrin (acryloyl-CD) was synthesized according to the method as illustrated in FIG. 10. β-cyclodextrin (CD) was reacted with toluenesulfonic anhydride (Ts2O) thereby to obtain tosyl CD. An azide of the tosyl CD was formed with sodium azide (NaN3) and then aminated with triphenylphosphine (PPh3). The amino compound thus obtained was further reacted with acryloyl chloride in a carbonate buffer solution thereby synthesizing acryloyl-6-amino-6-deoxy-β-cyclodextrin (acryloyl-CD).
<Production of Optically Active Molecule-Introduced Stimulus-Responsive Gel (EDANS-Introduced BPA-Responsive Gel)>

Figure 11:
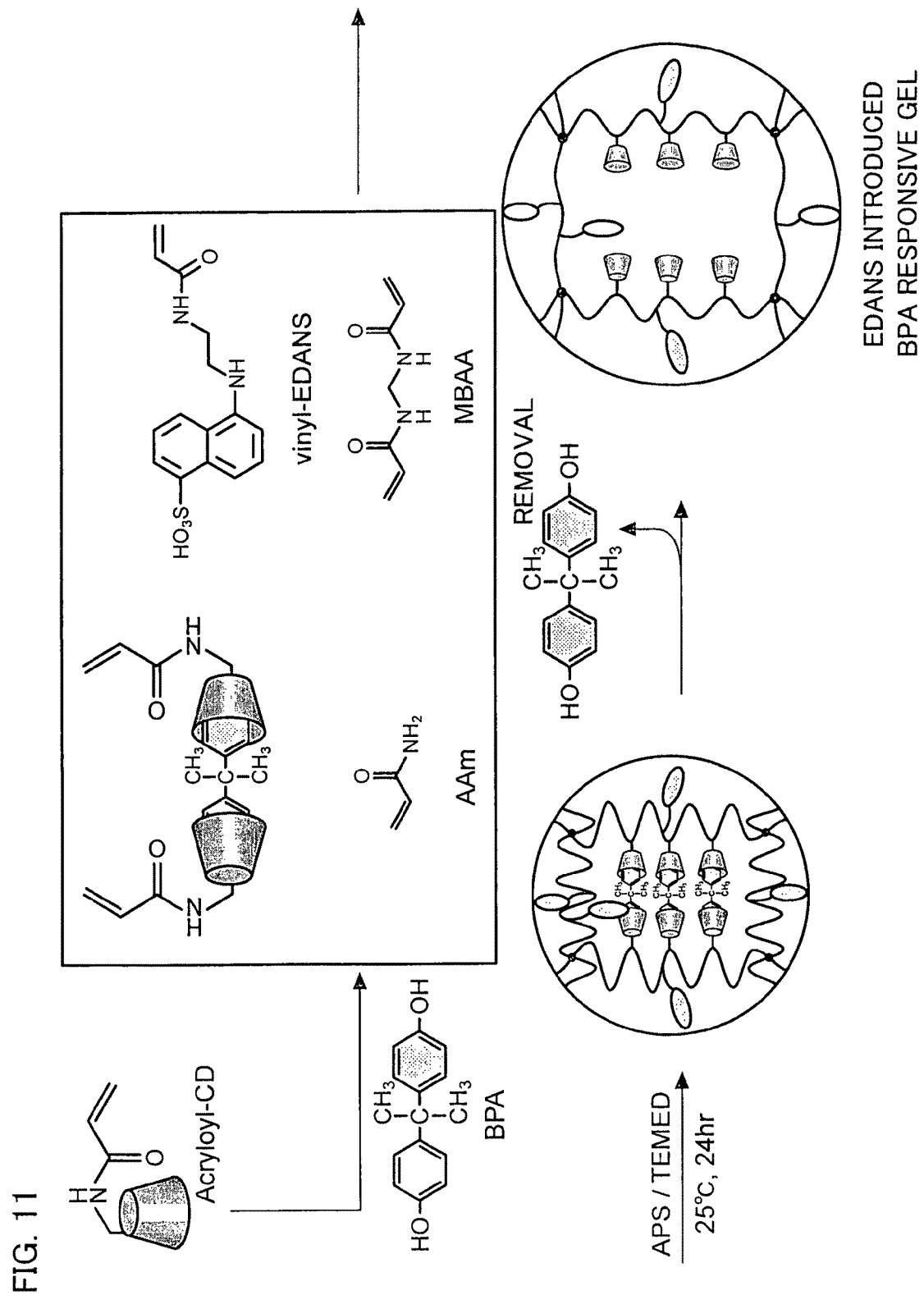
FIG. 11 is a view illustrating a method of producing the stimulus-responsive gel with optically active molecules introduced therein (BPA-responsive gel with EDANS-introduced therein) in Example, the stimulus-responsive gel being responsive to bisphenol A.

Next, a stimulus-responsive gel was prepared in the manner illustrated in FIG. 11. Acryloyl-CD of 220 mg and bisphenol A (BPA) of 21.5 mg, which was to be used as a template, were dissolved in distilled water of 1928 µl thereby forming clathrate acryloyl-CD with BPA trapped therein. After that, 130 mg of acrylamide (AAm) and 0.58 mg of vinyl-EDANS as monomers, 100 µl of N,N'-methylenebisacrylamide (MBAA) of a concentration of 1 mg/ml as a cross-linking agent, 50 ml of 0.1M ammonium peroxide (APS) and 50 µl of 0.8M N,N,N'N'-tetramethylethylenediamine (TEMED) as initiators were added to the clathrate acryloyl-CD with BPA trapped therein. Then, copolymerization was performed with the mixture at 25° C. for 24 hours. The synthesis of vinyl-EDANS used herein was carried out in the same manner as in Example 1. Moreover, the production of the gel was carried out by using a capillary tube made of glass, thereby to produce a cylinder-shaped gel. The gel thus produced was immersed in 30% acetone aqueous solution thereby to remove the template BPA sufficiently. Then, the gel was swollen to equilibrium in distilled water. Thereby, EDANS-introduced BPA-responsive gel was prepared, which was the targeted optically active molecule-introduced stimulus-responsive gel with optically active molecule introduced therein. The EDANS-introduced BPA-responsive gel thus prepared had a structure, as schematically illustrated in FIG. 11, in which acryloyl-CD and fluorescence-emitting vinyl-EDANS (indicated by ellipsoids in FIG. 11) are immobilized in a network structure of the polymer gel. If the EDANS-introduced BPA-responsive gel of this arrangement is in the presence of bisphenol A, which is a target molecule, clathrate acyloyl-CD with bisphenol A trapped therein is formed. Thereby, as illustrated in the schematic view illustrating a state before the removal of the template BPA in FIG. 11, the network structure of the gel is crossed linked via two acryloyl-CD and bisphenol A trapped therebetween. As it is known that the swelling ratio of a polymer gel is generally decreased as cross-linking concentration of the polymer is increased, it was expected that the bisphenol A responsive gel would shrink in the presence of bisphenol A, which was the target molecule and would increase cross-linking.

Example 7

Measurement of Volume Change in Optically Active Molecule-Introduced Stimulus-Responsive Gel (EDANS-Introduced BPA-Responsive Gel)

The stimulus-responsive gel (EDANS-introduced BPA-responsive gel) produced in Example 6 was immersed in a bisphenol aqueous solution (120 mg/l) and measured in its volume change. The volume change was worked out by measuring a change in the diameter of the gel over time from 0 hour at which the EDANS-introduced BPA-responsive gel was immersed in the bisphenol aqueous solution, and calculating its swelling ratio (volume change) using Equation (11).

Figure 12:
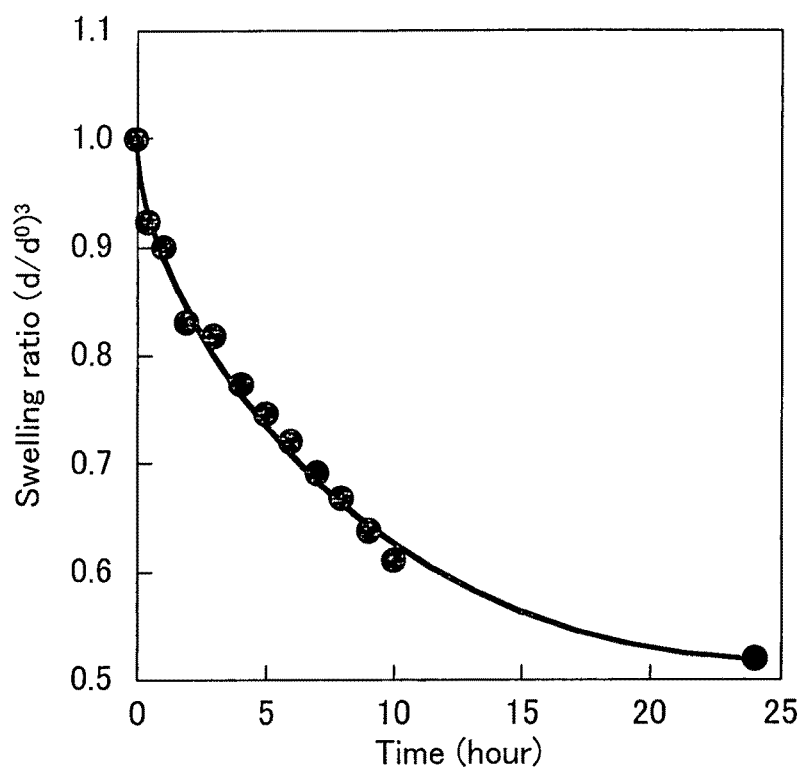
FIG. 12 is a graph illustrating how a swelling ratio (volume change) of a cylinder-shaped BPA-responsive gel with EDANS-introduced therein changed over time in Example, when the cylinder-shaped BPA-responsive gel was immersed in a bisphenol A aqueous solution.

FIG. 12 illustrates the change in the swelling ratio (volume change) over time in the cylinder-shaped EDANS-introduced BPA-responsive gel immersed in the bisphenol aqueous solution. In FIG. 12, the vertical axis indicates the swelling ratio (volume change) and the horizontal axis indicates time (hour). As illustrated in FIG. 12, the swelling ratio of the EDANS-introduced BPA-responsive gel was gradually reduced over time after the immersion. That is, the EDANS-introduced BPA-responsive gel shrank in the bisphenol aqueous solution gradually.

Example 8

Observation of Fluorescence Emitting Characteristic and Measurement of Fluorescence Intensity in Optically Active Molecule-Introduced Stimulus-Responsive Gel of Cylinder Shape Next, in order to study the relationship between the swelling ratio (volume change) and the fluorescence intensity of the gel, the EDANS-introduced BPA-responsive gel was immersed in the bisphenol aqueous solution and observed by fluorescent microscopic observation, which was carried out in the same way as in Example 4.

Figure 13:
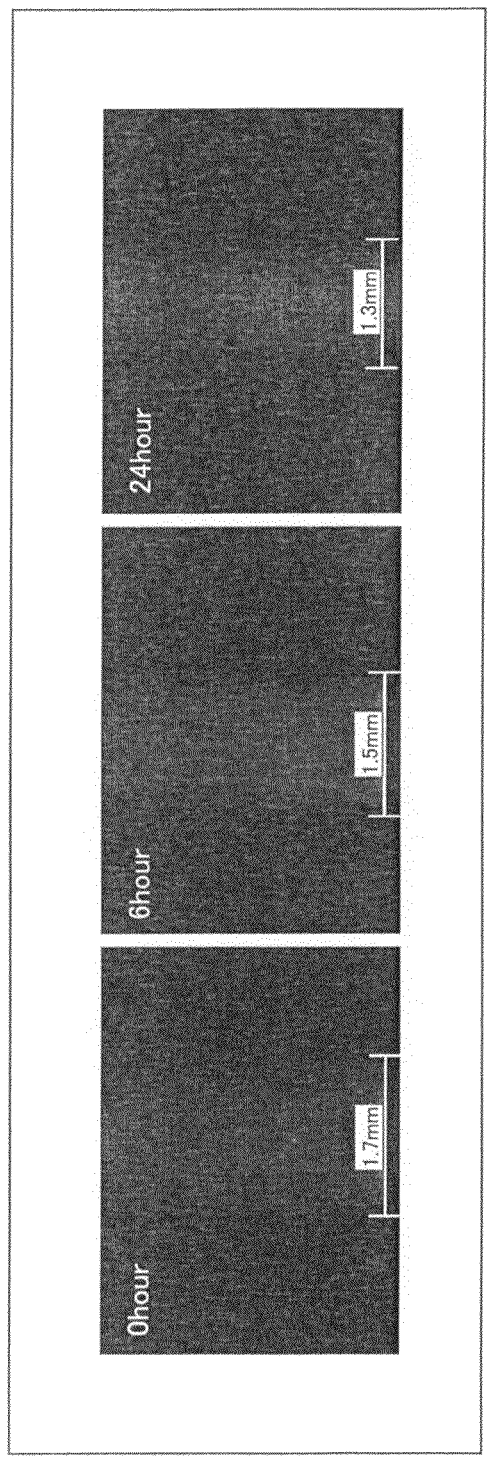
FIG. 13 is a view illustrating results of fluorescent microscopic observation of the BPA-responsive gel with EDANS-introduced therein at 0 hour, 6 hour, and 24 hour after immersing the BPA-responsive gel in the bisphenol A aqueous solution in Example.

FIG. 13 illustrates results of the fluorescent microscopic observation of the EDANS-introduced BPA-responsive gel at 0 hour, 6 hour, and 24 hour from the immersion. As illustrated in FIG. 13, the shrinkage of the EDANS-introduced BPA-responsive gel over time increased the fluorescence intensity of the EDANS-introduced BPA-responsive gel in the fluorescent microscopic pictures. It is deduced that the increase in the fluorescence intensity associated with the shrinkage of the EDANS-introduced BPA-responsive gel occurred due to an increase in the concentration of EDANS as a result of the volume reduction of the BPA-responsive gel with constant absolute quantity of the fluorescence-emitting EDANS in the gel. Thus, the microscopic pictures were subjected to image analysis thereby to calculate out the relative fluorescence intensity in the same way as in Example 4, in order to study the relationship between the swelling ratio (volume change) and the fluorescence intensity of the gel.

Figure 14:
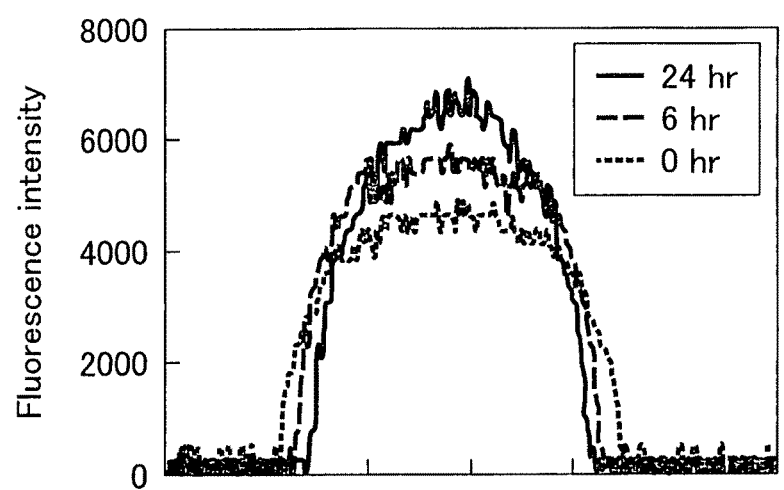
FIG. 14 is a view is fluorescence intensity of the BPA-responsive gel with EDANS-introduced therein, which gel was immersed in the bisphenol A aqueous solution, the fluorescence intensity being calculated out via image analysis of a fluorescent microscopic picture.

FIG. 14 illustrates the relative fluorescence intensity of the EDANS-introduced BPA-responsive gel immersed the bisphenol aqueous solution, the relative fluorescence intensity being calculated out via the image analysis of the fluorescence microscopic picture. The relative fluorescence intensity is a ratio of brightness (F0) of the gel in the pure water over brightness (F) of the gel in the bisphenol aqueous solution, the brightness being worked out by the image analysis. In FIG. 14, the vertical axis indicates the relative fluorescence intensity. As illustrated in FIG. 14, the relative fluorescence intensity was highest at a center of the gel, and increased over time.

Figure 15:
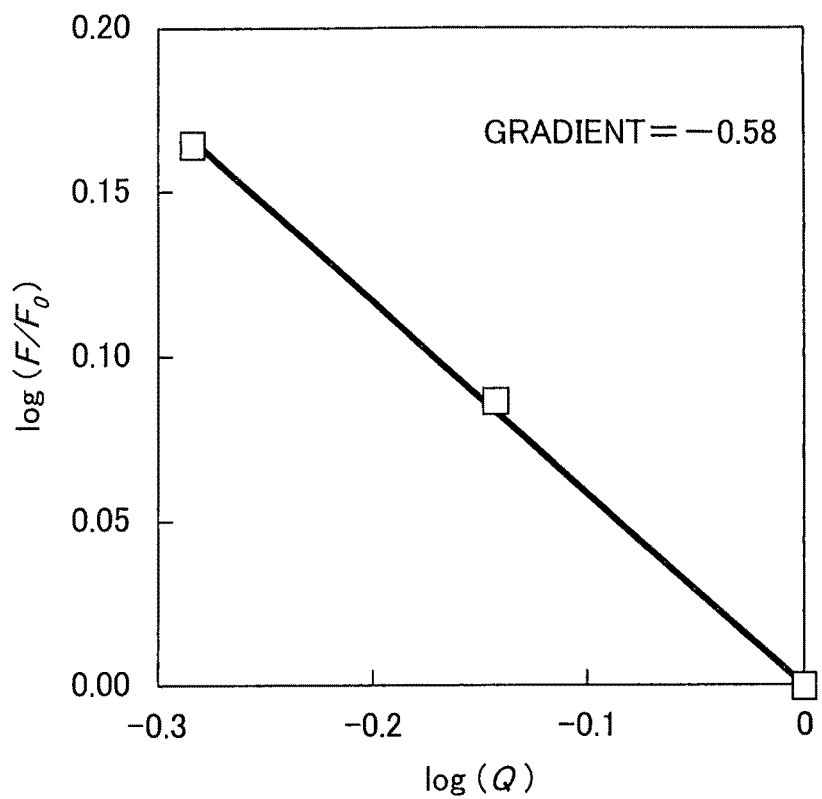
FIG. 15 is a graph plotting the fluorescence intensity against swelling ratio (volume change) of the BPA-responsive gel with EDANS-introduced therein.

FIG. 15 illustrates the relationship between the relative fluorescence intensity thus obtained and the swelling ratio (volume change) of the EDANS-introduced BPA-responsive gel. In FIG. 15, the vertical axis indicates the logarithms of the relative fluorescence intensity (F/F0), while the horizontal axis indicates the logarithms of the swelling ratio (volume change). As illustrated in FIG. 15, there was a clear linear relationship between the logarithms of the swelling ratio (volume change) and logarithms of the fluorescence intensity, and the straight line had a gradient of −0.58. That is, it was proved that there is a strong correlation between the swelling ratio (volume change) and the fluorescence intensity of the EDANS-introduced BPA-responsive gel, and that the volume of the EDANS-introduced BPA-responsive gel can be data-converted into the fluorescence intensity.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

A stimulus-responsive gel of the present invention comprises, as described above, a molecule having a fluorescence chromophore or a molecule capable of absorbing visible light or ultraviolet light. Because of this, a volume change of the stimulus-responsive gel by and according to the external stimulus can be converted into optical data in a form of a change in fluorescence intensity or absorption. Thus, the stimulus-responsive gel can be used as a simple system in a sensor element or the like. Therefore, the stimulus-responsive gel is applicable to contaminant detection in the environmental field, new diagnosis system capable of detecting/measuring a biomolecule indicative of a disease in the medical filed, and the like. Accordingly, the present invention is not only applicable but also very beneficial to various chemical industries such as pharmaceutical producing industries and industrial chemical industries, medical industries, and the like.

The invention claimed is:

1. A method of measuring an external stimulus and a volume change in a sensor element, the method comprising:

(a) creating an analytical curve by plotting logarithms of the volume change against logarithms of fluorescence intensity or absorbance of the visible light or ultraviolet light, by (i) exposing a sensor element to external stimuli of different known ionic concentration, and a liquid, wherein the sensor element comprises a stimulus-responsive gel comprising polyacrylic acid, wherein the stimulus-responsive gel comprises optically active molecules, which are 5-(2'-aminoethyl)aminonaphthalene-1-sulfonate (EDANS), wherein the stimulus responsive gel changes its volume in response to an external stimulus and the sensor element converts into optical data a volume change in the stimulus-responsive gel, and wherein the liquid is absorbed in or discharged out of the sensor element in response to the external stimuli, so as to cause volume changes in the sensor element, (ii) measuring the volume change in the sensor element exposed to the respective external stimuli of different known ionic concentrations, (iii) irradiating light of a particular wavelength on the sensor element exposed to the respective external stimuli of the different known ionic concentrations, and (iv) measuring fluorescence intensity or absorbance of visible light or ultraviolet light therein;

(b) (i) exposing the sensor element to an external stimulus of an unknown ionic concentration in the presence of the liquid, (ii) irradiating the light of the particular wavelength on the sensor element exposed to the external stimuli of the unknown ionic concentration, and (iii) measuring the fluorescence intensity or the absorbance of the visible light or the ultraviolet light in the sensor element; and (c) determining how large the volume change in the sensor element and the external stimulus of the unknown ionic concentration are, from the measured fluorescence intensity or the absorbance of the visible light or ultraviolet light by using the analytical curve.

2. The method as set forth in claim 1, wherein a concentration of the optically active molecules in the stimulus-responsive gel is in a range between about 0.01% w/w to about 10% w/w relative to the dried weight of the stimulus-responsive gel comprising the optically active molecules.

3. The method as set forth in claim 1, wherein the optically active molecules are chemically bonded to the polyacrylic acid forming the stimulus-responsive gel.

4. The method as set forth in claim 1, wherein the stimulus-responsive gel changes its volume by swelling or shrinking in response to the external stimulus by absorbing or discharging a liquid, wherein the liquid comprises water or an organic solvent.

5. The method as set forth in claim 1, wherein the concentration of optically active molecules in the stimulus-responsive gel is in a range between about 0.1% w/w to about 5% w/w relative to the dried weight of the stimulus-responsive gel comprising the optically active molecules.

6. The method as set forth in claim 1, wherein the logarithms of the volume change in the stimulus-responsive gel and the logarithms of the fluorescence intensity or absorbance of the visible light or ultraviolet light have a linear relationship.

* * * * *